(12) United States Patent
Gee et al.

(10) Patent No.: US 8,318,502 B2
(45) Date of Patent: Nov. 27, 2012

(54) LONG WAVELENGTH FLUOROGENIC INTRACELLULAR ION INDICATORS THAT ARE WELL RETAINED IN THE CYTOSOL

(75) Inventors: Kyle Gee, Springfield, OR (US); Vladimir Martin, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 429 days.

(21) Appl. No.: 12/602,973

(22) PCT Filed: Jun. 5, 2008

(86) PCT No.: PCT/US2008/065986
§ 371 (c)(1),
(2), (4) Date: Dec. 3, 2009

(87) PCT Pub. No.: WO2008/151303
PCT Pub. Date: Dec. 11, 2008

(65) Prior Publication Data
US 2010/0330584 A1    Dec. 30, 2010

Related U.S. Application Data

(60) Provisional application No. 60/942,163, filed on Jun. 5, 2007.

(51) Int. Cl.
*G01N 33/50* (2006.01)
*C07D 273/01* (2006.01)
*C07D 311/90* (2006.01)
*C07D 491/147* (2006.01)

(52) U.S. Cl. ............. 436/79; 436/73; 436/74; 540/468; 546/48; 549/392; 549/394

(58) Field of Classification Search .............. 436/73, 436/74, 79; 546/48; 540/468; 549/392, 549/393
See application file for complete search history.

(56) References Cited

U.S. PATENT DOCUMENTS
2005/0250214 A1* 11/2005 Gee .................................. 436/84

FOREIGN PATENT DOCUMENTS
GB   2372749       7/2003
WO   WO-2008/151303   12/2008

OTHER PUBLICATIONS

PCT/US08/065986; International Search Report and Written Opinion mailed Aug. 27, 2008.
Frederik, et al., "Tracing of labile zinc in live fish hepatocytes using Fluozin-3", *BioMetals*, vol. 19, No. 4, Aug. 1, 2006; pp. 437-450.
Gee, Kyle R. et al., "Chemical and Physiological Characterization of fluo-4 Ca2+ indicator dyes", *Cell Calcium*, 2000; pp. 97-106.
Martin, Vladimir V. et al., "Novel fluo-4 analogs for fluorescent calcium measurements", Cell Calcium, vol. 36, 2004; pp. 509-514.

* cited by examiner

*Primary Examiner* — Bernard Dentz

(57) ABSTRACT

Cell permeable metal ion indicator compounds and methods of their use and synthesis are described. The compound comprises a metal chelating moiety ($M_c$), a reporter molecule and two or more lipophilic groups ($G_L$) covalently bonded through a linker to the reporter molecule, wherein the lipophilic groups, when present in a live cell, are cleaved resulting in two or more negatively charged groups.

45 Claims, 4 Drawing Sheets

LONG WAVELENGTH FLUOROGENIC INTRACELLULAR ION INDICATORS THAT ARE WELL RETAINED IN THE CYTOSOL

FIELD OF THE INVENTION

The present invention provides intracellular ion indicator compounds capable of chelating and detecting metal ions in cells. The compounds generally comprise a metal chelating moiety ($M_c$), a reporter molecule and one or more lipophilic groups ($G_L$) covalently bonded to the reporter molecule, wherein the lipophilic groups, when present in a live cell, are cleaved resulting in one or more negatively charged groups.

BACKGROUND OF THE INVENTION

Metal ions such as calcium are involved in many cellular processes including signal transduction. Small variances in intracellular ion levels can have a major impact on cellular processes. Measurement of ion levels provides a very sensitive method for identifying various cellular activities.

Several fluorescent calcium indicators known in art are employed in biological research and high throughput screening. Generally, long wavelength indicators, such as rhodamine-based compounds bear a positive charge. Positively charged molecules compartmentalize in cell mitochondria. Because calcium ion release in activated cells happens in the cytosol, positively charged indicators show a weak response to calcium ion influx. Alternatively, fluorescein-based indicators have also been described that avoid accumulation in the mitochondria, yet have a shorter wavelength with less optimal emission spectra. Several calcium ion indicators are described in: Haugland, R. P. *Handbook of Fluorescent Probes and Research Products*, 9th Ed, Molecular Probes: Eugene, Oreg., 2002, Chapter 20; Martin et al., *Cell Calcium* 2004, 36, 509-14; and Beierlein et al., *J. Neurophysiol.* 2004, 92, 591-599.

Free cytosolic calcium ions play a key role in many aspects of cellular signalling and regulation, and fluorogenic calcium indicators like Fluo-4 (Invitrogen Corp.) provide quantitative and spatial information on calcium gradients with microscopic and plate reader measurements. Currently, green channel indicators like Fluo-4 enjoy a centerpiece role in a variety of investigative methodologies and HTS assays at Gi, Go, and Gs coupled G Protein Coupled Receptors (GPCRs).

Shifting the excitation of the fluorescent calcium indicator toward longer wavelengths would be beneficial for imaging applications by making it possible to multiplex the dye with existing green fluorophores and fluorescent protein constructs. It could also improve readout in HTS assays by shifting to wavelengths where compound library autofluorescence is less of a problem.

A need exists for compounds which have the advantage of a longer wavelength and avoid localization in the mitochondria. Furthermore, a need exists for fluorogenic probes that are taken up by cells and provide sensitive detection of cytosolic metal ions, such as calcium, when in the cell. Here we report the development and evaluation of a novel fluorescent calcium indicators having better loading and response characteristics than existing longer-wavelength calcium indicators.

SUMMARY OF THE INVENTION

The invention involves the use of dye molecules having a cleavable lipophilic group that masks negative charges on the dye. Upon cellular internalization, the lipophilic groups are cleaved and the dye remains at the site of action. Particularly, the negative charges decrease the degree of mitochondrial localization.

The synthetic methods used in this invention are flexible and allow introduction of a several extra acidic groups, which unlike the carboxylates on certain dyes (such as BAPTA) serve the purpose of positive charge compensation, rather than participation in the chelate formation.

Also, because of extra negative charges, the compounds are less prone to leak into extracellular environment. The synthesis of low leaking indicators is a task of general importance. Therefore, the scope of this invention also includes carboxylic derivative of calcium indicators having shorter-wavelength fluorophores.

Additionally, longwavelength indicators (generally having an emission spectra above about 530 nm) described herein avoid cellular autofluorescence and interference from other agents such as drugs which have been introduced to the cell. The long wavelength intracellular ion indicators also allow for detection in multiplexing applications, such as with GFP's or other indicators/dyes.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1 depicts a spectroscopic study of the calcium binding to compound 145 ($\lambda_{ex}$=555 nm, $\lambda_{em}$=580 nm; $K_d$=380 nmol), wherein FIG. 2 depicts Imaging of cellular localization of, wherein

DETAILED DESCRIPTION

Introduction

The present invention is based upon the phenomenon in which the optical properties of a fluorophore can be modulated by strategic covalent attachment of a metal ion-binding moiety (a chelator). Certain ion chelators reduce the fluorescence of the fluorophore by a through-space or through-bond interaction known as PET (photoinduced electron transfer), in which fluorescence is inhibited by interaction of the excited state fluorophore with an electron-rich chelator moiety. As the chelator moiety binds metal ion(s), the PET effect is diminished, resulting in increased fluorescence from the fluorophore.

This phenomenon has been employed in many commercially available intracellular ion indicators, most notably in the detection of intracellular calcium ions. However, these indicators each have their advantages and disadvantages. The green indicators are typically based on a fluorescein dye and as such are well retained in the cytosol (due to the overall negative charge) but have limited ability to be multiplexed with other intracellular reporter molecules due to spectral overlap. The longer wavelength intracellular ion indicators are typically based on rhodamine, or other dyes comprising one or more positive charges, that preferentially localize to specific organelles such as the mitochondria, resulting in poor ion detection in the cytosol.

Figure 2A:
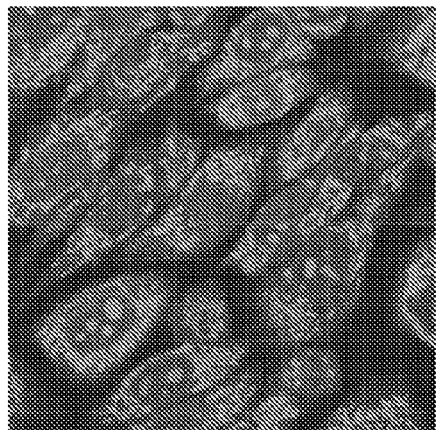
FIG. 2A shows conventional red Ca indicator Rhod-2 (mitochondrial localization)
Figure 2B:
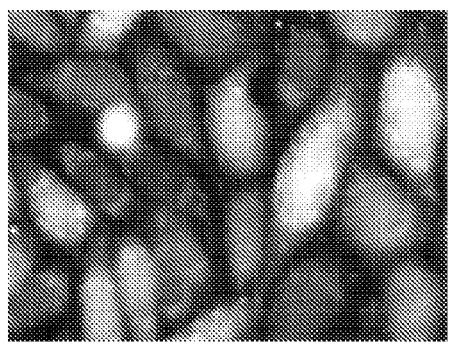
FIG. 2B shows compound 146 (red cytosolic signal)
Figure 2C:
FIG. 2C shows cytosolic indicator Fluo-4 (green cytosolic signal).

Herein we report on novel intracellular ion indicators that have a long wavelength emission spectra and are also well retained in the cytosol, making it possible for the first time to accurately measure cytosolic ion concentration in a multiplexed assay such as with Green Fluorescent Protein (GFP) or other well know green intracellular ion indicators. Our invention is based, in part, on the strategic placement of labile lipophilic groups on the dye portion of the intracellular ion indicator. While red ion indicators such as Rhod-2 comprise lipophilic groups the resulting negative charges on the chelating moiety of the compound is not enough to retain the compound in the cytosol. We have found, unexpectedly, that by adding labile lipohilic groups, such as AM esters, to the fluorophore portion of the compound that these ion indicators are retained in the cytosol and not targeted to the mitochondria (FIG. 2).

The invention addresses the molecular design of fluorescent intracellular ion indicators intended for intracellular detection of such ions. Introduction of extra negatively charged groups, such as carboxylic acidic moieties into the indicator molecules resulted in an overall signal increase due to cytosolic localization/retention. Before cytosolic localization however, negative charges can inhibit or preclude cellular internalization. Accordingly, addition of labile lipophilic groups that are cleaved upon cellular internalization permitted traversal of the plasma membrane. The compounds described herein are more effective at localizing to the cytosol for ion detection than existing indicators and have an emission spectra longer than about 530 nm to about 800 nm.

DEFINITIONS

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a metal chelator" includes a plurality of chelators and reference to "a cell" includes a plurality of cells and the like.

Unless defined otherwise, all technical and scientific terms used herein have the same meaning as commonly understood by one of ordinary skill in the art to which this invention is related. The following terms are defined for purposes of the invention as described herein.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose an appropriate method for a particular situation. See, generally, Furniss et al. (eds.), VOGEL'S ENCYCLOPEDIA OF PRACTICAL ORGANIC CHEMISTRY $5^{TH}$ ED., Longman Scientific and Technical Ltd., Essex, 1991, pp. 809-816; and Heller, *Acc. Chem. Res.* 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —$CH_2O$— is intended to also recite —$OCH_2$—.

Any of the "substituted" groups may comprise a lipophilic group ($G_L$).

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3$)($CH_3CH_2$)CH—), t-butyl (($CH_3)_3C$—), n-pentyl ($CH_3CH_2CH_2CH_2CH_2$—), and neopentyl (($CH_3)_3CCH_2$—).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups —NRC(O)alkyl, —NRC(O)substituted alkyl, —NRC(O)cycloalkyl, —NRC(O)substituted cycloalkyl, —NRC(O)cycloalkenyl, —NRC(O)substituted cycloalkenyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic wherein R is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —$NH_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cylcoalkyl, —$SO_2$-cycloalkenyl, —$SO_2$-substituted cycloalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' nor R" are hydrogen.

"Aminocarbonyl" refers to the group —C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group —C(S)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonylamino" refers to the group —NRC(O)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —NRC(S)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonyloxy" refers to the group —O—C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group —SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group —O—SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonylamino" refers to the group —NR—SO$_2$NR'R" where R is hydrogen or alkyl and $R^{10}$ and $R^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkyenyl, aryl, substituted aryl, heteroaryl, substituted heteroaryl, heterocyclic and substituted heterocyclic are as defined herein.

"Amidino" refers to the group —C(=Na''')R'R" where R', R", and R''' are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified, for example, by vinyl, allyl, and but-3-en-1-yl.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO₃H, substituted sulfonyl, sulfonyloxy, thioacyl, thiol, alkylthio, and substituted alkylthio, wherein said substituents are defined herein and with the proviso that any hydroxy substitution is not attached to a vinyl (unsaturated) carbon atom.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO₃H, substituted sulfonyl, sulfonyloxy, thioacyl, thiol, alkylthio, and substituted alkylthio, wherein said substituents are defined herein and with the proviso that any hydroxy substitution is not attached to an acetylenic carbon atom.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —NR—C(O)O-alkyl, substituted —NR—C(O)O-alkyl, —NR—C(O)O-alkenyl, —NR—C(O)O-substituted alkenyl, —NR—C(O)O-alkynyl, —NR—C(O)O-substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic wherein R is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, substituted —O—C(O)O-alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO₃H, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH₂.

"Substituted guanidino" refers to —NR¹³C(=NR¹³)N(R¹³)₂ where each R¹³ is independently selected from the group consisting of hydrogen, alkyl, substituted alkyl, aryl, substituted aryl, heteroaryl, substituted heteroaryl, heterocyclic, and substituted heterocyclic and two R¹³ groups attached to a common guanidino nitrogen atom are optionally joined together with the nitrogen bound thereto to form a heterocyclic or substituted heterocyclic group, provided that at least one $R^{13}$ is not hydrogen, and wherein said substituents are as defined herein.

"H" indicates hydrogen.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or unsaturated group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Hydrazinyl" refers to the group —NHNH$_2$— or =NNH—.

"Substituted hydrazinyl" refers to a hydrazinyl group, wherein a non-hydrogen atom, such as an alkyl group, is appended to one or both of the hydrazinyl amine groups. An example of substituted hydrazinyl is —N(alkyl)-NH$_2$ or =N$^+$ (alkyl)-NH$_2$.

"Nitro" refers to the group —NO$_2$.

"Oxo" refers to the atom (=O) or (—O$^-$).

"Spirocyclyl" refers to divalent saturated cyclic group from 3 to 10 carbon atoms having a cycloalkyl or heterocyclyl ring with a spiro union (the union formed by a single atom which is the only common member of the rings) as exemplified by the following structure:

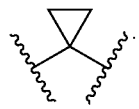

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cylcoalkyl, —OSO$_2$-cycloalkenyl, —OSO$_2$-substituted cycloalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thiol" refers to the group —SH.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

A dashed line projecting from a substituent, such as:

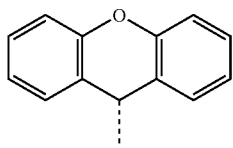

indicates the point of attachment to the base molecule. For a fused ring, dashed lines indicate portions of the base molecule where the fused ring is attached, such as:

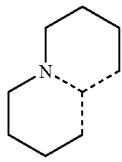

wherein the full molecule could have the structure:

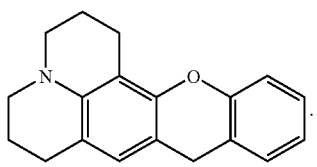

"Stereoisomer" or "stereoisomers" refer to compounds that differ in the chirality of one or more stereocenters. Stereoisomers include enantiomers and diastereomers.

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moeity such as pyrazoles, imidazoles, benzimidazoles, triazoles, and tetrazoles.

"Calcium sensitive dye" refers to a compound whose fluorescent properties are affected, preferably increased, by the presence and coordination of calcium ions.

The term "ion sensitive dye" as used herein refers to a compound whose fluorescent properties are affected, preferably increased, by the presence and coordination of particular ions.

The term "intracellular ion sensitive dye", "fluorogenic ion indicator", or "fluorogenic intracellular ion indicator" are used interchangeably and as used herein refer to a present compound comprising a reporter molecule and chelator moiety wherein the reporter molecule is appended with one or more labile lipophilic groups. Preferably the reporter molecule has an emission spectra longer than about 530 nm.

"Patient," "subject" or "individual" refers to mammals and includes humans and non-human mammals, such as monkeys, dogs, cats, horses, cows, pocket pets, pigs or rats.

"Salt" refers to acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

The terms "protein" and "polypeptide" are used herein in a generic sense to include polymers of amino acid residues of any length. The term "peptide" is used herein to refer to polypeptides having less than 250 amino acid residues, typically less than 100 amino acid residues. The terms apply to amino acid polymers in which one or more amino acid residues are an artificial chemical analogue of a corresponding naturally occurring amino acid, as well as to naturally occurring amino acid polymers.

The term "reactive group" as used herein refers to a group that is capable of reacting with another chemical group to form a covalent bond, i.e. is covalently reactive under suitable reaction conditions, and generally represents a point of attachment for another substance. The reactive group is a moiety, such as carboxylic acid or succinimidyl ester, on the compounds of the present invention that is capable of chemically reacting with a functional group on a different compound to form a covalent linkage. Reactive groups generally include nucleophiles, electrophiles and photoactivatable groups.

Exemplary reactive groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds., *Organic Functional Group Preparations*, Academic Press, San Diego, 1989).

The term "dye" as used herein refers to a compound that emits light to produce an observable detectable signal.

The term "carrier molecule" as used herein refers to a biological or a non-biological component that is covalently bonded to a compound of the present invention. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof.

The term "Linker" or "L", as used herein, refers to a single covalent bond or a series of stable covalent bonds incorporating 1-20 nonhydrogen atoms selected from the group consisting of C, N, O, S and P that covalently attach the fluorogenic or fluorescent compounds to another moiety such as a chemically reactive group or a biological and non-biological component. Exemplary linking members include a moiety that includes —C(O)NH—, —C(O)O—, —NH—, —S—, —O—, and the like. A "cleavable linker" is a linker that has one or more cleavable groups that may be broken by the result of a reaction or condition. The term "cleavable group" refers to a moiety that allows for release of a portion, e.g., a fluorogenic or fluorescent moiety, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., *Biochem. Biophys. Acta,* 761: 152-162 (1983); Joshi et al., *J. Biol. Chem.*, 265: 14518-14525 (1990); Zarling et al., *J. Immunol.*, 124: 913-920 (1980); Bouizar et al., *Eur. J. Biochem.*, 155: 141-147 (1986); Park et al., *J. Biol. Chem.*, 261: 205-210 (1986); Browning et al., *J. Immunol.*, 143: 1859-1867 (1989). Moreover a broad range of cleavable, bifunctional (both homo- and hetero-bifunctional) spacer arms are commercially available.

An exemplary cleavable group, an ester, is cleavable group that may be cleaved by a reagent, e.g. sodium hydroxide, resulting in a carboxylate-containing fragment and a hydroxyl-containing product.

The linker can be used to attach the compound to another component of a conjugate, such as a targeting moiety (e.g., antibody, ligand, non-covalent protein-binding group, etc.), an analyte, a biomolecule, a drug and the like.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

The term "affinity" as used herein refers to the strength of the binding interaction of two molecules, such as a metal chelating compound and a metal ion or a positively charged moiety and a negatively charged moiety.

The term "aqueous solution" as used herein refers to a solution that is predominantly water and retains the solution characteristics of water. Where the aqueous solution contains solvents in addition to water, water is typically the predominant solvent.

The term "cell permeable" as used herein refers to compounds of the present invention that are able to cross the cell membrane of live cells. Lipophilic groups that are covalently attached to the present compounds, facilitate this permeability and live cell entry. Once inside the cells, the lipophilic groups are hydrolyzed resulting in charged molecules that are well retained in living cells. Particularly useful lipophilic groups include acetoxymethyl (AM) ester and acetate esters wherein once inside the cells the groups are cleaved by nonspecific esterases resulting in charged molecules.

The term "complex" as used herein refers to the association of two or more molecules, usually by non-covalent bonding.

The term "detectable response" as used herein refers to a change in or an occurrence of, a signal that is directly or indirectly detectable either by observation or by instrumentation and the presence or magnitude of which is a function of the presence of a target metal ion in the test sample. Typically, the detectable response is an optical response resulting in a change in the wavelength distribution patterns or intensity of absorbance or fluorescence or a change in light scatter, fluorescence quantum yield, fluorescence lifetime, fluorescence polarization, a shift in excitation or emission wavelength or a combination of the above parameters. The detectable change in a given spectral property is generally an increase or a decrease. However, spectral changes that result in an enhancement of fluorescence intensity and/or a shift in the wavelength of fluorescence emission or excitation are also useful. The change in fluorescence on ion binding is usually due to conformational or electronic changes in the indicator that may occur in either the excited or ground state of the fluorophore, due to changes in electron density at the ion binding site, due to quenching of fluorescence by the bound target metal ion, or due to any combination of these or other effects. Alternatively, the detectable response is an occurrence of a signal wherein the fluorophore is inherently fluorescent and does not produce a change in signal upon binding to a metal ion or biological compound.

The term "fluorophore" as used herein refers to a composition that is inherently fluorescent or demonstrates a change in fluorescence upon binding to a biological compound or metal ion, or metabolism by an enzyme, i.e., fluorogenic. Fluorophores may be substituted to alter the solubility, spectral properties or physical properties of the fluorophore. Numerous fluorophores are known to those skilled in the art and include, but are not limited to coumarin, acridine, furan, dansyl, cyanine, pyrene, naphthalene, benzofurans, quinolines, quinazolinones, indoles, benzazoles, borapolyazaindacenes, oxazine and xanthenes, with the latter including fluoresceins, rhodamines, rosamine and rhodols as well as other fluorophores described in RICHARD P. HAUGLAND, MOLECULAR PROBES HANDBOOK OF FLUORESCENT PROBES AND RESEARCH CHEMICALS ($9^{th}$ edition, including the CD-ROM, September 2002). The fluorophore moiety may be substituted by substituents that enhance solubility, live cell permeability and alter spectra absorption and emission.

The term "kit" as used refers to a packaged set of related components, typically one or more compounds or compositions.

The term "lipophilic group" as used herein refers to substituents which modify the charge or polarity of functionalities, such as an amino, thiol, hydroxyl, sulfonate or carboxylate group, thereby rendering them more hydrophobic.

Preferred protecting groups for use in the present invention include groups which reduce or eliminate the charge on the parent compound rendering it more lipophilic, and are also capable of being cleaved, preferably in vivo by enzymes, such as esterases. One preferred protecting group is an acetoxymethyl (AM) ester or an analog thereof. Additional groups groups include, but are not limited to, substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate; and silyl ethers such as those obtained by reaction of a hydroxyl group with a reagent such as, but not limited to, t-butyldimethyl-chlorosilane, trimethylchlorosilane, triisopropylchlorosilane, triethylchlorosilane. Modification to amine groups include, but are not limited to, AM esters, amides such as, formamide, acetamide, trifluoroacetamide, and benzamide; imides, such as phthalimide, and dithiosuccinimide; and others. Modified sulfhydryl groups include, but are not limited to, thioethers such as S-benzyl thioether, and S-4-picolyl thioether; substituted S-methyl derivatives such as hemithio, dithio and aminothio acetals; and others.

The term "metal chelator" or "metal chelating compound" as used herein refers to a chemical compound that combines with a metal ion to form a chelate ring structure.

The term "metal ion" or "target metal ion" as used herein refers to any metal cation that is capable of being chelated by a metal chelating compound. Typically, these metal ions are physiological and or nutritional relevant metal ion such as $Na^+$, $K^+$, $Zn^{2+}$, $Mg^{2+}$, $Fe^{2+}$, and $Ca^{2+}$. The term metal ion used herein also refers to the metal ions $Ga^{3+}$, $Tb^{3+}$, $La^{3+}$, $Pb^{2+}$, $Hg^{2+}$, $Cd^{2+}$, $Cu^{2+}$, $Ni^{2+}$, $Co^{2+}$, $Mn^{2+}$, $Ba^{2+}$, and $Sr^{2+}$. Preferably the metal ion includes those that are present in the cytosol of a biological cell such as calcium, sodium, potassium, magnesium, zinc and iron. Also included are metal ions that can act as a surrogate for a physiological important metal ion, such as thallium, rubidium or lithium which can act as a surrogate for potassium The term "PET linker" refers to a linker as defined above, which affects photoinduced electron transfer (PET) between the chelator and dye moieties. The PET linker is preferably a covalent bond. In another embodiment the PET linker is an alkylene spacer between the chelating moiety and the reporter moiety, thus limiting the interaction between the ion sensor and reporter to the PET mechanism. Such linkers are described more thoroughly in US Patent Publication No. 2006-0024833, U.S. Pat. Nos. 6,124,135; 6,359,135; He et al. Chem. Soc. (2003) 125:1468-1469; and He et al. Anal. Chem. (2003) 75:3549-55, which are incorporated by reference (with respect to their disclosure of linkers, dyes and/or metal ion chelators) as if set forth fully herein.

The term "photoinduced electron transfer (PET)" as used herein refers to intramolecular electron transfer.

The term "reporter molecule" as used herein refers to a fluorophore or dye, terms that are defined above, which comprise part of the present intracellular ion indicators.

The term "sample" as used herein refers to any material that may contain target metal ions, as defined above. Typically, the sample is a live cell or a biological fluid that comprises endogenous host cell proteins. Alternatively, the sample may be a buffer solution or an environmental sample containing target metal ions. The sample may be in an aqueous solution, a viable cell culture or immobilized on a solid or semi solid surface such as a polyacrylamide gel, membrane blot or on a microarray.

The term "Stokes shift" as used herein refers to the difference in wavelength between absorbed and emitted energy. Specifically, the Stokes shift is the difference (usually in frequency units) between the spectral positions and the band maxima (or band origin) of the absorption and luminescence arising from the same electronic transitions.

Unless numbered, or proper claim construction (e.g. antecedent basis) requires it, multiple steps in a method or process claim/embodiment are not required to be performed sequentially.

The Compounds

In general, for ease of understanding the present invention, the metal ion binding compounds and corresponding substituents will first be described in detail, followed by the many and varied methods in which the compounds find uses, which is followed by exemplified methods of use and synthesis of certain novel compounds that are particularly advantageous for use with the methods of the present invention.

The present compounds find utility in binding intracellular ions, in particular calcium ions in a sample. The sample includes live cells or a biological fluid that comprises live cells and endogenous host cell proteins, buffer solutions and environmental samples. The sample may also comprise synthetic or artificial membranes or lipid bilayers. Therefore, the present compounds, when comprising a reporter molecule (typically a fluorophore or dye) find utility in binding, isolating, quantitating, monitoring, sequestering and detecting intracellular metal ions wherein the detectable signal is modulated by photoinduced electron transfer (PET). As described herein detection of the intracellular metal ions is accomplished in live cells wherein the present compound comprises one or more labile lipophilic groups, such as an AM or acetate ester that allows for entry across the live cell membrane, on the reporter molecule of the present compounds. Once inside the cells nonspecific esterases cleave the AM or acetate ester resulting in a charged molecule that is well retained in the cell. These present compounds are particularly useful for binding physiologically relevant levels of cytosolic metal ions.

The present compounds consist of three functional elements, metal ion chelating moiety ($M_c$), the reporter molecule (fluorescent dye or other moiety listed herein) and one or more lipophilic groups covalently bonded to the reporter molecule through a linker wherein the lipophilic groups, when present in a live cell, are cleaved resulting in one or more negatively charged groups. One distinguishing feature of these compounds is one or more lipophilic groups ($G_L$) located on the reporter/dye molecule. The groups provide a number of technical advantages, including increased internalization in the cell, decreased "leaking" out of the cell, decreased localization in the mitochondria of the cell, use of reporter molecule skeletons that are typically neutral or positively charged, long wavelength cytosolic ion indicators, ability to multiplex with shorter wavelength intracellular indicators, and thereby increased sensitivity for detection of cellular activities/processes.

In a more specific embodiment, the present compound binds and detects calcium ions wherein a detectable response is a result of photoinduced electron transfer (PET) and the compound comprises a metal chelating moiety and a fluorophore or dye that is covalently bonded to the metal chelating moiety by a PET linker, such as a covalent bond or $-(CR_2)_n-NR'-$ or $-(CR_2)_n-$ wherein R and R' are independently selected from the group consisting of hydrogen, alkyl, and substituted alkyl and n is 1-10. When the linker is $-(CR_2)_n-$ the terminal carbon atom of the linker must be directly and covalently bonded to a nitrogen atom of the fluorophore.

In some embodiments, the present compounds exhibit a Stokes shift that is greater than about 20 nm, 50 nm, or greater than about 100 nm, or greater than about 150 nm.

One preferred compound involves an intracellular ion indicator compound, wherein the compound comprises a metal chelating moiety ($M_c$), a reporter molecule (DYE) and two or more lipophilic groups ($G_L$) covalently bonded through a linker to the reporter molecule, wherein the lipophilic groups, when present in a live cell, are cleaved resulting in two or more negatively charged groups. In another embodiment thereof, the metal chelating moiety ($M_c$) is covalently bonded through a PET linker to the reporter molecule. In another embodiment, the reporter molecule is a fluorescent dye. In another embodiment, the lipophilic groups comprise an ester. More particularly, the two or more negatively charged groups are carboxylate groups. In another embodiment, the lipophilic groups are selected from the group consisting of $C_1$-$C_6$ carboxyalkyl, —$(CH_2)_{1-6}COOCR^{15}{}_2OC(=O)(CH_2)_{0-4}CH_3$, and alpha-acyloxyalkyl; wherein $R^{15}$ is H, alkyl or substituted alkyl. In another embodiment, the lipophilic groups are —$CH_2CH_2COOCH$—$_2OC(=O)CH_3$. In another embodiment the fluorescent dye comprises at least three or at least four lipophilic groups. In another embodiment the fluorescent dye comprises 2, 3, 4, 5, or 6 lipophilic groups. In another embodiment, the DYE is selected from the group consisting of a xanthene, borapolyazaindacene, cyanine, benzofuran, quinazolinone, indole, benzazole, oxazine, and a coumarin. In a preferred embodiment the DYE is a long wavelength such as those with an emission spectra longer than about 530 nm to 800 nm.

In another embodiment, the intracellular ion indicator compound has the structure:

$$(G_L)_v\text{-L-DYE-}M_c$$

wherein,
L is a linker;
$G_L$ is a lipophilic group;
DYE is a reporter molecule;
$M_c$ is a metal chelating moiety; and
v is 2, 3, 4, or 5; or
v is 1, and DYE is a rhodamine a 3,6-diaminoxanthene (rhodamine).

In another embodiment, the intracellular ion indicator compound has the structure:

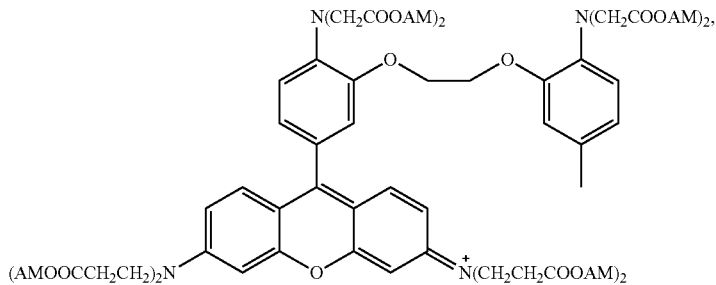

146

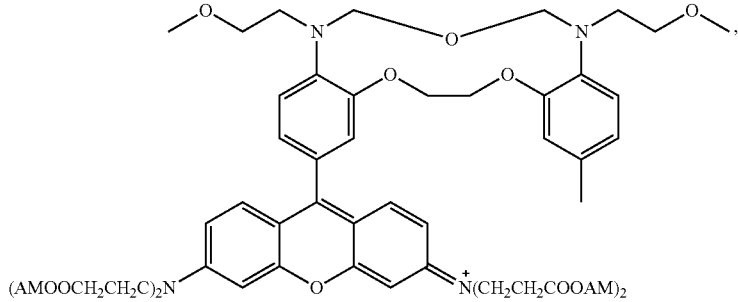

154

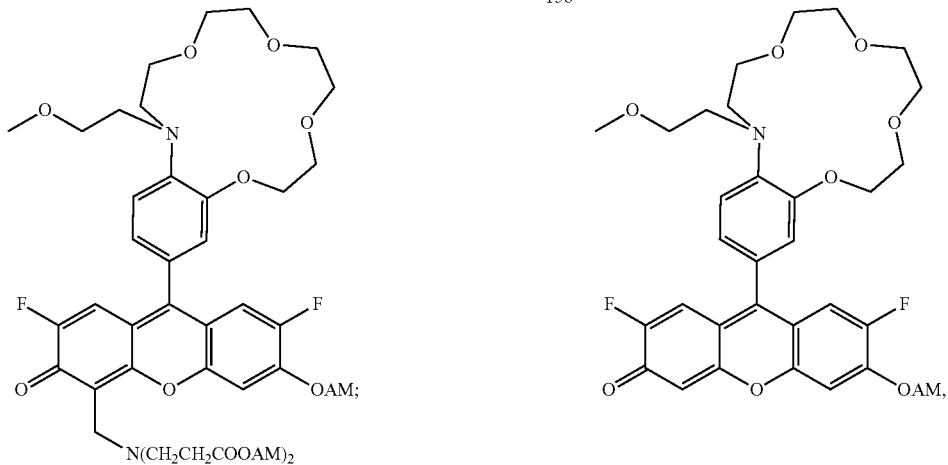

158

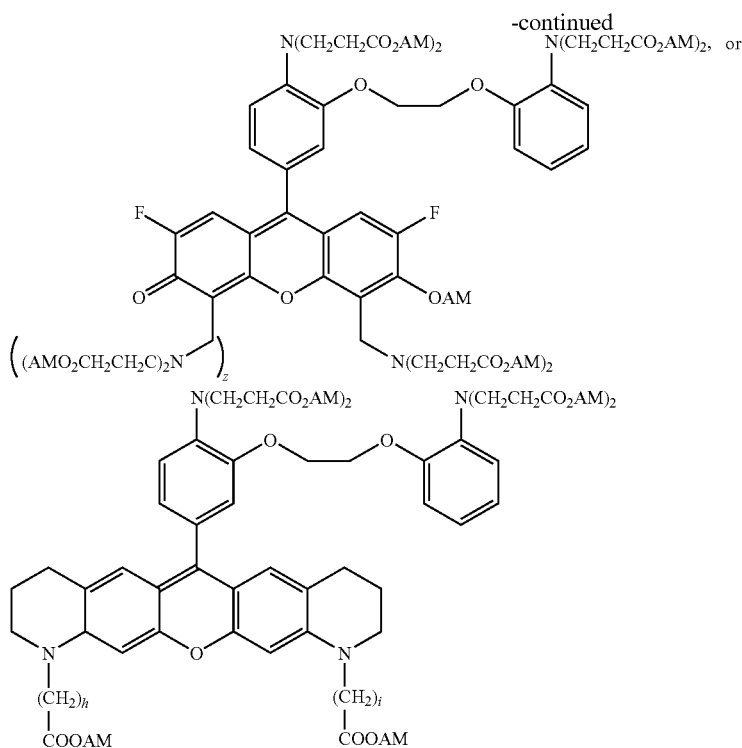

wherein h and i are independently 0-4;
z is 0 or 1; and
AM is —CH$_2$OC(=O)CH$_3$.

In another embodiment of the invention, the intracellular ion indicator further comprises a reactive group, carrier molecule or solid support. These substituents can be attached to the reporter molecule, the metal chelating moiety, provided they do not interfere with the coordination of the metal ions, or to the linker.

Chelating Moiety

The ion-sensing or chelating moiety of the present compound is a moiety that will bind or chelate metal ions. Typically this results in a change in the fluorescent signal. Metal ions of the present invention, include but are not limited to, Ca$^{2+}$, Zn$^{2+}$, Mg$^{2+}$, Ga$^{3+}$, Tb$^{3+}$, La$^{3+}$, Pb$^{2+}$, Hg$^{2+}$, Cd$^{2+}$, Cu$^{2+}$, Ni$^{2+}$, Co$^{2+}$, Fe$^{2+}$, Mn$^{2+}$, Ba$^{2+}$, and Sr$^{2+}$. In one aspect the metal ion is a physiological relevant ion selected from the group consisting of Ca$^{2+}$, Mg$^{2+}$, Fe$^{2+}$ and Zn$^{2+}$. In a further aspect the metal ion is Ca$^{2+}$, which is most notably chelated by the well-known BAPTA chelating moiety. In other embodiments, the metal ion is chelated by a crown ether, cryptan, APTRA (aminophenol triacetic acid) especially for coordinating Mg$^{2+}$, FluoZin-1, 2 or 3 or a phenanthroline, for example:

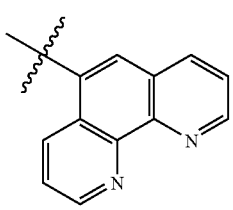

which may be further substituted.

The term "BAPTA" as used herein refers to a metal-chelating compound that is 1,2-bis(2-aminophenoxy)ethane-N,N,N',N'-tetraacetic acid or its analogs, derivatives, ring-fused variants and conjugates, and all metallic and nonmetallic salts, partial salts and hydrates thereof, including any corresponding compounds disclosed in U.S. Pat. Nos. 4,603,209; 4,849,362; 5,049,673; 5,453,517; 5,459,276; 5,516,911; 5,501,980; 6,162,931 and 5,773,227. When used generically, "BAPTA" refers to two benzene rings that are joined by a C$_1$-C$_3$ hydrocarbon bridge terminated by oxygen atoms, including methylenedioxy (—OCH$_2$O—), ethylenedioxy (—OCH$_2$CH$_2$O—) or propylenedioxy (—OCH$_2$CH$_2$CH$_2$O) bridging groups, where each benzene ring is optionally substituted by one or more substituents that adjust the metal ion-binding affinity, solubility, chemical reactivity, spectral properties or other physical properties of the compound. BAPTA derivatives additionally include compounds in which the benzene rings of the BAPTA structure are substituted by or fused to additional aromatic, or heteroaromatic rings. In one embodiment the chelating group or BAPTA is substituted with a reactive group, carrier molecule, or solid support.

In one embodiment, the chelating moiety (M$_c$) is capable of binding intracellular metal ion. In another embodiment, M$_c$ comprises BAPTA or a crown ether moiety. More particularly, M$_c$ has the structure:

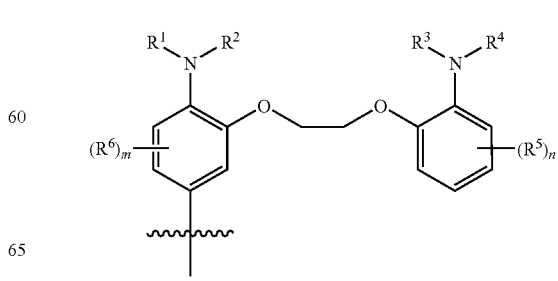

wherein, $R^1$, $R^2$, $R^3$ and $R^4$ are each independently selected from the group consisting of carbonyl, substituted carbonyl, carboxyl, alkyl, substituted alkyl, reactive group, carrier molecule, solid support, and -L-$(G_L)_w$; or $R^2$ and $R^4$ are bound together by: —$(CH_2CH_2$—$O)_t$—$CH_2CH_2$—, wherein t is 1 or 2;

$R^5$ and $R^6$ are each independently selected from the group consisting of -L-$(G_L)_w$, alkyl, substituted alkyl, carbonyl, substituted carbonyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, reactive group, carrier molecule, solid support, and substituted heterocyclyl;

L is a linker;

$G_L$ is a lipophilic group;

w is 1 or 2; and m and n are each independently 0, 1, 2, or 3.

In a more particular embodiment thereof, n is 1 and $R^5$ is —$CH_3$. In another embodiment, $R^2$ and $R^4$ are bound together by: —$CH_2CH_2$—O—$CH_2CH_2$—. In another embodiment, $R^1$, $R^2$, $R^3$ and $R^4$ are -L-$(G_L)_w$. In another embodiment, L is a single covalent bond, or a covalent linkage that is linear or branched, cyclic or heterocyclic, saturated or unsaturated, having 1-30 nonhydrogen atoms selected from the group consisting of C, N, P, O and S; and are composed of any combination of ether, thioether, amine, ester, carboxamide, sulfonamide, hydrazide bonds and aromatic or heteroaromatic bonds. In another embodiment, L is -oxo-, alkoxy, -amino-, or -substituted amino-.

In another embodiment, $M_c$ has the structure:

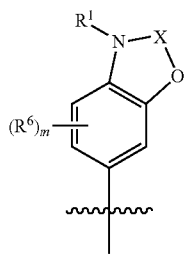

wherein,

X is —$(CH_2CH_2$—$O)_y$—$CH_2CH_2$—, wherein y is 1, 2, 3, 4, or 5;

$R^1$ is H, alkyl, substituted alkyl, carbonyl, reactive group, carrier molecule, solid support, or substituted carbonyl;

$R^6$ is selected from the group consisting of -L-$(G_L)_w$, alkyl, substituted alkyl, carbonyl, substituted carbonyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, reactive group, carrier molecule, solid support, and substituted heterocyclyl;

L is a linker;

w is 1 or 2;

$G_L$ is a lipophilic group; and m is 0, 1, 2, or 3.

The present invention also provides zinc-binding compounds and methods for the selective binding and detection of physiological concentrations of zinc ions. The zinc-binding compounds find utility in binding (sequestering), detecting (monitoring and/or quantitating) free zinc ions. Detection also includes the screening of drug candidates that affect intracellular zinc ion concentrations, ion channels and zinc-binding proteins).

The metal chelating moiety of the zinc-binding compound is an analog of the well-known calcium chelator, BAPTA (1,2-bis(2-aminophenoxy)ethane-N,N,N',N'-tetraacetic acid), wherein the chelating moiety has been modified from a tetraacetic acid moiety to a triacetic, diacetic or monoacetic acid moiety. This change in acetic acid groups on the metal chelating moiety results in the selective binding of zinc ions in the presence of calcium ions, both of which are present in biological fluids and intracellular cytosolic fluid and organelles. Due to the relatively high concentration of physiological intracellular calcium compared to zinc and the fact that BAPTA binds calcium with higher affinity than zinc, BAPTA is an ineffective chelator for binding physiological zinc ions in the presence of calcium ions. However, we found that by lowering the affinity for calcium that triacetic acid analog of BAPTA chelating moieties preferentially bind zinc in the presence of calcium ions at physiological concentrations of both ions.

Accordingly, one particular embodiment of the present invention involves detection or monitoring for both zinc and calcium ions in the cytosol of a cell, wherein at least two different intracellular ion indicators are introduced to the cell and wherein each indicator comprises a dye which is separately detectable from the other.

Reporter Molecule

The reporter molecule of the present invention functions as a reporter molecule to confer a detectable signal, directly or indirectly, to the intracellular metal ions. This results in the ability to detect, monitor and quantitate target metal ions in a sample.

The present reporter molecules can be any reporter molecule known to one skilled in the art. A wide variety of chemically reactive fluorescent dyes that may be suitable for incorporation into the compounds of the invention are already known in the art (RICHARD P. HAUGLAND, MOLECULAR PROBES HANDBOOK OF FLUORESCENT PROBES AND RESEARCH PRODUCTS (2002)). Reporter molecules include, without limitation, a fluorophore, a dye, or a tandem dye (energy transfer pair). Preferably, the reporter molecule is a fluorophore wherein when the present compounds are non-fluorescent until bound by a metal ion, i.e. fluorogenic. After binding a metal ion and upon illumination with an appropriate wavelength the compound produces a detectable signal modulated by PET.

Where the detectable response is a fluorescence response, it is typically a change in fluorescence, such as a change in the intensity, excitation or emission wavelength, distribution of fluorescence, fluorescence lifetime, fluorescence polarization, or a combination thereof. Preferably, the detectable optical response upon binding a target ion is a change in fluorescence intensity that is greater than approximately 150% relative to the same compound in the absence of the metal ion, more preferably greater than 5-fold, and most preferably more that 10-fold.

A fluorescent dye of the present invention is any chemical moiety that exhibits an absorption maximum beyond 280 nm, and when covalently linked to a metal chelating moiety of the present invention, forms a present fluorogenic metal ion-binding compound with an emission spectra longer than about 530 nm. A preferred embodiment for detecting intracellular ions in live cells is a fluorogenic ion-binding compound wherein the reporter molecule is fluorophore wherein the fluorophore is appended with one or more lipophilic groups. Most preferably are fluorescent dyes that emit beyond the green portion of the spectrum (above 530 nm).

Dyes of the present invention include those derivatives that emit longer than about 530 nm. These dyes and dye derivatives include, without limitation, a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a carbocyanine (including any corresponding compounds in U.S. Ser. Nos. 09/557,275; 09/968,401 and 09/969,853 and U.S. Pat. Nos. 6,403,807; 6,348,599; 5,486,616; 5,268,486; 5,569,587; 5,569,766; 5,627,027 and 6,048,982), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774, 339; 5,187,288; 5,248,782; 5,274,113; and 5,433,896), a xanthene (including any corresponding compounds disclosed in U.S. Pat. Nos. 6,162,931; 6,130,101; 6,229,055; 6,339,392; 5,451,343 and U.S. Ser. No. 09/922,333), an oxazine or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including an corresponding compounds disclosed in U.S. Pat. Nos. 4,603,209 and 4,849,362) and benzphenalenone (including any corresponding compounds disclosed in U.S. Pat. No. 4,812,409) and derivatives thereof. As used herein, oxazines include resorufins (including any corresponding compounds disclosed in U.S. Pat. No. 5,242,805), aminooxazinones, diaminooxazines, and their benzo-substituted analogs.

Where the dye is a xanthene, the dye is preferably a rhodamine or rhodol (in conjunction with a phenyl on the metal chelator ($M_c$) including any corresponding compounds disclosed in U.S. Pat. Nos. 5,227,487 and 5,442,045), a rosamine or a rhodamine (including any corresponding compounds in U.S. Pat. Nos. 5,798,276; 5,846,737; 5,847,162; 6,017,712; 6,025,505; 6,080,852; 6,716,979; 6,562,632). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171).

Preferred dyes of the invention include dansyl, xanthene, cyanine, borapolyazaindacene, pyrene, naphthalene, coumarin, oxazine and derivatives thereof. Preferred xanthenes are aminoxanthene (rhodamine or rhodol) and derivatives thereof, BODIPY and dansyl.

Typically the dye contains one or more aromatic or heteroaromatic rings, that are optionally substituted one or more times by a variety of substituents, including without limitation, halogen, nitro, sulfo, cyano, alkyl, perfluoroalkyl, alkoxy, alkenyl, alkynyl, cycloalkyl, arylalkyl, acyl, aryl or heteroaryl ring system, benzo, or other substituents typically present on chromophores or fluorophores known in the art.

In an exemplary embodiment, the dyes are independently substituted by substituents selected from the group consisting of hydrogen, halogen, amino, substituted amino, alkyl, substituted alkyl, aryl, substituted aryl, heteroaryl, substituted heteroaryl, alkoxy, sulfo, reactive group and carrier molecule. In another embodiment, the xanthene dyes of this invention comprise both compounds substituted and unsubstituted on the carbon atom of the central ring of the xanthene by substituents typically found in the xanthene-based dyes such as phenyl and substituted-phenyl moieties. Most preferred dyes are rhodamine, rhodol, and derivatives thereof. The choice of the dye attached to the chelating moiety will determine the metal ion-binding compound's absorption and fluorescence emission properties as well as its live cell properties, i.e. ability to localize to the cytosol.

In another preferred embodiment, the fluorescent dye comprises a 3-aminoxanthene or a tautomer thereof. In another embodiment, the fluorescent dye comprises a 3,6-diaminoxanthene or a tautomer thereof.

In another embodiment, the fluorescent dye has the structure:

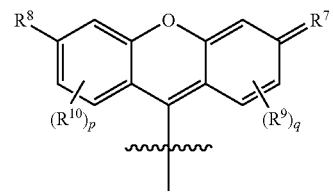

wherein, $R^9$ and $R^{10}$ are each independently selected from the group consisting of alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, substituted heterocyclyl, reactive group, carrier molecule, solid support and -L-$(G_L)_w$;

$R^7$ is =O or =N$(R^{11})_2$, wherein $R^{11}$ is H, alkyl, $(G_L)_w$, substituted alkyl, carbonyl, reactive group, carrier molecule, solid support or substituted carbonyl;

$R^8$ is hydroxyl, —O$R_{13}$ or —N$(R^{12})_2$ wherein $R^{12}$ and $R^{13}$ are independently H, alkyl, $(G_L)_w$, substituted alkyl, carbonyl, reactive group, carrier molecule, solid support or substituted carbonyl;

or one or both of $R^8$ and $(R^{10})_p$ and $R^7$ and $(R^9)_q$ are taken together to form a fused aryl or heteroaryl group;

L is a linker;

$G_L$ is a lipophilic group;

w is 1 or 2; and p and q are each independently 0, 1 or 2;

wherein the dye comprises at least two $G_L$ groups.

In another embodiment, $R^7$ is =O, $R^8$ is hydroxyl, p+q=1 and $R^9$ or $R^{10}$ is -L-$(G_L)_w$. In another embodiment, $R^9$ is -L-$(G_L)_w$ and q is 1.

In another embodiment, L is a single covalent bond, or a covalent linkage that is linear or branched, cyclic or heterocyclic, saturated or unsaturated, having 1-30 nonhydrogen atoms selected from the group consisting of C, N, P, O and S;

and are composed of any combination of ether, thioether, amine, ester, carboxamide, sulfonamide, hydrazide bonds and aromatic or heteroaromatic bonds. In another embodiment, L is alkyl, substituted alkyl, -oxo-, alkoxy, -amino-, or -substituted amino-.

In another embodiment, $R^7$ is =$N^+(G_L)_2$ and $R^8$ is —$OG_L$. In another embodiment, $R^7$ is =$N^+(G_L)_2$ and $R^8$ is —$N(G_L)_2$. More particularly, $G_L$ is —$(CH_2)_{1-6}COOCR^{15}{}_2OC(=O)(CH_2)_{0-4}CH_3$ wherein $R^{15}$ is H, alkyl or substituted alkyl. More particular still, $G_L$ is —$CH_2CH_2COOCH_2OC(=O)CH_3$.

In another embodiment, the fluorescent dye has the structure:

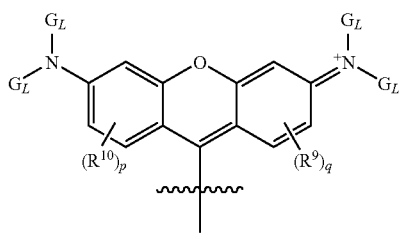

$R^9$ and $R^{10}$ are each independently selected from the group consisting of alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, substituted heterocyclyl and -L-$(G_L)_w$;

L is a linker;
$G_L$ is a lipophilic group;
w is 1 or 2; and
p and q are each independently 0, 1 or 2.

In another embodiment thereof, $G_L$ comprises an ester. More particularly, $G_L$ is selected from the group consisting of $C_1$-$C_6$ carboxyalkyl, —$(CH_2)_{1-6}COOCR^{15}{}_2OC(=O)(CH_2)_{0-4}CH_3$, and alpha-acyloxyalkyl; wherein $R^{15}$ is H, alkyl or substituted alkyl. More particularly, $G_L$ is: —$CH_2CH_2COOCH_2OC(=O)CH_3$.

In another embodiment, the fluorescent dye is selected from the group consisting of a xanthene, borapolyazaindacene, cyanine, benzofuran, quinazolinone, indole, benzazole, oxazine, and a coumarin. More particularly, the dye is a xanthene.

Linkers

The above described substituents are covalently attached to the chelating moiety or reporter moiety of the present compounds via a linker. In particular these substituents include a solid support, carrier molecule or reactive group wherein they may be directly attached (where Linker is a single bond) to the moieties (chelator or reporter) or attached through a series of stable bonds. When the linker is a series of stable covalent bonds the linker typically incorporates 1-30 nonhydrogen atoms selected from the group consisting of C, N, O, S and P. When the linker is not a single covalent bond, the linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. Typically the linker incorporates less than 15 nonhydrogen atoms and are composed of any combination of ether, thioether, thiourea, amine, ester, carboxamide, sulfonamide, hydrazide bonds and aromatic or heteroaromatic bonds. Typically the linker is a combination of single carbon-carbon bonds and carboxamide, sulfonamide or thioether bonds. The bonds of the linker typically result in the following moieties that can be found in the linker: ether, thioether, carboxamide, thiourea, sulfonamide, urea, urethane, hydrazine, alkyl, aryl, heteroaryl, alkoky, cycloalkyl and amine moieties. Examples of a linker include substituted or unsubstituted polymethylene, arylene, alkylarylene, arylenealkyl, or arylthio.

In one embodiment, the linker contains 1-6 carbon atoms; in another, the linker comprises a thioether linkage. Exemplary linking members include a moiety that includes —C(O)NH—, —C(O)O—, —NH—, —S—, —O—, and the like. In another embodiment, the linker is or incorporates the formula —$(CH_2)_d(CONH(CH_2)_e)_z$— or where d is an integer from 0-5, e is an integer from 1-5 and z is 0 or 1. In a further embodiment, the linker is or incorporates the formula —O—$(CH_2)$—. In yet another embodiment, the linker is or incorporates a phenylene or a 2-carboxy-substituted phenylene.

Any combination of linkers may be used to attach the carrier molecule, solid support or reactive group and the present compounds together. The linker may also be substituted to alter the physical properties of the reporter molecule or chelating moiety, such as spectral properties of the dye.

Another important feature of the linker is to provide an adequate space between the carrier molecule, reactive group or solid support and the chelating moiety or reporter moiety so as to prevent steric hinderance. Therefore, the linker of the present compound is important for (1) attaching the carrier molecule, reactive group or solid support to the compound, (2) providing an adequate space between the carrier molecule, reactive group or solid support and the compound so as not to sterically hinder the action of the compound and (3) for altering the physical properties of the present compounds.

Reactive Groups

In another exemplary embodiment of the invention, the present compounds are chemically reactive, and are substituted by at least one reactive group. The reactive group functions as the site of attachment for another moiety, such as a carrier molecule or a solid support, wherein the reactive group chemically reacts with an appropriate reactive or functional group on the carrier molecule or solid support. Thus, in another aspect of the present invention the compounds comprise the chelating moiety, linker, reporter molecule, a reactive group moiety and optionally a carrier molecule and/or a solid support.

In an exemplary embodiment, the compounds of the invention further comprise a reactive group which is a member selected from an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In a particular embodiment the reactive group is selected from the group consisting of carboxylic acid, succinimidyl ester of a carboxylic acid, hydrazide, amine and a maleimide. In exemplary embodiment, at least one member selected from $R^1$, $R^2$, $R^3$, $R^4$, $R^5$, $R^6$, $R^7$, $R^8$, $R^9$, $R^{10}$, $R^{11}$, $R^{12}$ and $R^{13}$ comprise a reactive group, carrier molecule or solid support. Preferably, at least one of $R^1$, $R^2$, $R^3$, $R^4$, $R^5$, $R^6$, $R^7$, and $R^8$ is a reactive group, most preferred is at least one of $R^5$, $R^6$, $R^7$ or W. Alternatively, if the present compound comprises a carrier molecule or solid support a reactive group may be covalently attached independently to those substituents, allowing for further conjugation to a reporter molecule, carrier molecule or solid support.

In one aspect, the compound comprises at least one reactive group that selectively reacts with an amine group. This amine-reactive group is selected from the group consisting of succinimidyl ester, sulfonyl halide, tetrafluorophenyl ester and iosothiocyanates. Thus, in one aspect, the present compounds form a covalent bond with an amine containing molecule in a sample. In another aspect, the compound comprises at least one reactive group that selectively reacts with a thiol group. This thiol-reactive group is selected from the group consisting of maleimide, haloalkyl and haloacetamide (including any reactive groups disclosed in U.S. Pat. Nos. 5,362,628; 5,352,803 and 5,573,904).

These reactive groups are synthesized during the formation of the present compound and carrier molecule and solid support containing compounds to provide chemically reactive metal ion-binding compounds. In this way, compounds incorporating a reactive group can be covalently attached to a wide variety of carrier molecules or solid supports that contain or are modified to contain functional groups with suitable reactivity, resulting in chemical attachment of the components. In an exemplary embodiment, the reactive group of the compounds of the invention and the functional group of the carrier molecule or solid support comprise electrophiles and nucleophiles that can generate a covalent linkage between them. Alternatively, the reactive group comprises a photoactivatable group, which becomes chemically reactive only after illumination with light of an appropriate wavelength. Typically, the conjugation reaction between the reactive group and the carrier molecule or solid support results in one or more atoms of the reactive group being incorporated into a new linkage attaching the present compound of the invention to the carrier molecule or solid support. Selected examples of functional groups and linkages are shown in Table 1, where the reaction of an electrophilic group and a nucleophilic group yields a covalent linkage.

TABLE 1

Examples of some routes to useful covalent linkages

| Electrophilic Group | Nucleophilic Group | Resulting Covalent Linkage |
|---|---|---|
| activated esters* | amines/anilines | carboxamides |
| acrylamides | Thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | Hydrazines | hydrazones |
| aldehydes or ketones | hydroxylamines | oximes |
| alkyl halides | amines/anilines | alkyl amines |
| alkyl halides | Carboxylic acids | esters |
| alkyl halides | Thiols | thioethers |
| alkyl halides | alcohols/phenols | ethers |
| alkyl sulfonates | Thiols | thioethers |
| alkyl sulfonates | Carboxylic acids | esters |
| alkyl sulfonates | alcohols/phenols | ethers |
| anhydrides | alcohols/phenols | esters |
| anhydrides | amines/anilines | carboxamides |
| aryl halides | Thiols | thiophenols |
| aryl halides | Amines | aryl amines |
| aziridines | Thiols | thioethers |

TABLE 1-continued

Examples of some routes to useful covalent linkages

| Electrophilic Group | Nucleophilic Group | Resulting Covalent Linkage |
|---|---|---|
| boronates | Glycols | boronate esters |
| carbodiimides | Carboxylic acids | N-acylureas or anhydrides |
| diazoalkanes | Carboxylic acids | esters |
| epoxides | Thiols | thioethers |
| haloacetamides | Thiols | thioethers |
| haloplatinate | Amino | platinum complex |
| haloplatinate | heterocycle | platinum complex |
| haloplatinate | Thiol | platinum complex |
| halotriazines | amines/anilines | aminotriazines |
| halotriazines | alcohols/phenols | triazinyl ethers |
| halotriazines | Thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | Thiols | thioethers |
| phosphoramidites | Alcohols | phosphite esters |
| silyl halides | Alcohols | silyl ethers |
| sulfonate esters | amines/anilines | alkyl amines |
| sulfonate esters | Thiols | thioethers |
| sulfonate esters | Carboxylic acids | esters |
| sulfonate esters | Alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g., succinimidyloxy (—OC$_4$H$_4$O$_2$) sulfosuccinimidyloxy (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates Choice of the reactive group used to attach the compound of the invention to the substance to be conjugated typically depends on the reactive or functional group on the substance to be conjugated and the type or length of covalent linkage desired. The types of functional groups typically present on the organic or inorganic substances (biomolecule or non-biomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins.

Typically, the reactive group will react with an amine, a thiol, an alcohol, an aldehyde, a ketone, or with silica. Preferably, reactive groups react with an amine or a thiol functional group, or with silica. In one embodiment, the reactive group is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. No. 5,714,327.

Where the reactive group is an activated ester of a carboxylic acid, such as a succinimidyl ester of a carboxylic acid, a sulfonyl halide, a tetrafluorophenyl ester or an isothiocyanates, the resulting compound is particularly useful for preparing conjugates of carrier molecules such as proteins, nucleotides, oligonucleotides, or haptens. Where the reactive group is a maleimide, haloalkyl or haloacetamide (including any reactive groups disclosed in U.S. Pat. Nos. 5,362,628; 5,352,803 and 5,573,904 (supra)) the resulting compound is particularly useful for conjugation to thiol-containing substances. Where the reactive group is a hydrazide, the resulting compound is particularly useful for conjugation to periodate-oxidized carbohydrates and glycoproteins, and in addition is an aldehyde-fixable polar tracer for cell microinjection. Where the reactive group is a silyl halide, the resulting compound is particularly useful for conjugation to silica surfaces, particularly where the silica surface is incorporated into a fiber optic probe subsequently used for remote ion detection or quantitation.

In a particular aspect, the reactive group is a photoactivatable group such that the group is only converted to a reactive species after illumination with an appropriate wavelength. An appropriate wavelength is generally a UV wavelength that is less than 400 nm. This method provides for specific attachment to only the target molecules, either in solution or immobilized on a solid or semi-solid matrix. Photoactivatable reactive groups include, without limitation, benzophenones, aryl azides and diazirines.

Preferably, the reactive group is a photoactivatable group, succinimidyl ester of a carboxylic acid, a haloacetamide, haloalkyl, a hydrazine, an isothiocyanate, a maleimide group, an aliphatic amine, a silyl halide, a cadaverine or a psoralen. More preferably, the reactive group is a succinimidyl ester of a carboxylic acid, a maleimide, an iodoacetamide, or a silyl halide. In a particular embodiment the reactive group is a succinimidyl ester of a carboxylic acid, a sulfonyl halide, a tetrafluorophenyl ester, an iosothiocyanates or a maleimide.

Carrier Molecules

In any of the above embodiments, the compound can be covalently bound to a carrier molecule. If the compound has a reactive group, then the carrier molecule can alternatively be linked to the compound through the reactive group. The reactive group may contain both a reactive functional moiety and a linker, or only the reactive functional moiety.

A variety of carrier molecules are useful in the present invention. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, and polymers. In another exemplary embodiment, at least one member selected from $R^1$, $R^2$, $R^3$, $R^4$, $R^5$, $R^6$, $R^7$, $R^8$, $R^9$, $R^{10}$, $R^{11}$, $R^{12}$ or $R^{13}$ is a carrier molecule or is attached to a carrier molecule.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In a preferred embodiment the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In another preferred embodiment, the carrier molecule is an antibody or fragment thereof, an antigen, an avidin or streptavidin, a biotin, a dextran, an IgG binding protein, a fluorescent protein, agarose, and a non-biological microparticle.

In an exemplary embodiment, the enzymatic substrate is selected from an amino acid, peptide, sugar, alcohol, alkanoic acid, 4-guanidinobenzoic acid, nucleic acid, lipid, sulfate, phosphate, —$CH_2OCOalkyl$ and combinations thereof. Thus, the enzyme substrates can be cleave by enzymes selected from the group consisting of peptidase, phosphatase, glycosidase, dealkylase, esterase, guanidinobenzotase, sulfatase, lipase, peroxidase, histone deacetylase, endoglycoceramidase, exonuclease, reductase and endonuclease.

In another exemplary embodiment, the carrier molecule is an amino acid (including those that are protected or are substituted by phosphates, carbohydrates, or $C_1$ to $C_{22}$ carboxylic acids), or a polymer of amino acids such as a peptide or protein. In a related embodiment, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, or a growth factor. Exemplary haptens include biotin, digoxigenin and fluorophores.

In another exemplary embodiment, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In another exemplary embodiment, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In another exemplary embodiment, the carrier molecule comprises a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). In a related embodiment, the polysaccharide carrier molecule includes dextran, agarose or FICOLL.

In another exemplary embodiment, the carrier molecule comprises a lipid (typically having 6-25 carbons), including glycolipids, phospholipids, and sphingolipids. Alternatively, the carrier molecule comprises a lipid vesicle, such as a liposome, or is a lipoprotein (see below). Some lipophilic substituents are useful for facilitating transport of the conjugated dye into cells or cellular organelles.

Alternatively, the carrier molecule is a cell, cellular systems, cellular fragment, or subcellular particles, including virus particles, bacterial particles, virus components, biological cells (such as animal cells, plant cells, bacteria, or yeast), or cellular components. Examples of cellular components that are useful as carrier molecules include lysosomes, endosomes, cytoplasm, nuclei, histones, mitochondria, Golgi apparatus, endoplasmic reticulum and vacuoles.

In another exemplary embodiment, the carrier molecule non-covalently associates with organic or inorganic materials. Exemplary embodiments of the carrier molecule that possess a lipophilic substituent can be used to target lipid assemblies such as biological membranes or liposomes by non-covalent incorporation of the dye compound within the membrane, e.g., for use as probes for membrane structure or for incorporation in liposomes, lipoproteins, films, plastics, lipophilic microspheres or similar materials.

In an exemplary embodiment, the carrier molecule comprises a specific binding pair member wherein the present compounds are conjugated to a specific binding pair member and used to the formation of the bound pair. Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. In this instance, the dye compounds of the present invention function as a reporter molecule for the specific binding pair. Exemplary binding pairs are set forth in Table 2.

TABLE 2

Representative Specific Binding Pairs

| antigen | Antibody |
|---|---|
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |
| peptide | peptide receptor |
| protein | protein receptor |
| enzyme substrate | Enzyme |
| DNA (RNA) | cDNA (cRNA)† |
| hormone | hormone receptor |
| ion | Chelator |

*IgG is an immunoglobulin
†cDNA and cRNA are the complementary strands used for hybridization Solid Supports In an exemplary embodiment, the present compounds of the invention are covalently bonded to a solid support. The solid support may be attached to the compound either through the chelating moiety, reporter molecule or DYE, a substituent on the chelating moiety, reporter molecule or DYE, or through a reactive group, if present, or through a carrier molecule, if present. Even if a reactive group, reporter molecule and/or a carrier molecule are present, the solid support may be attached through the chelating moiety. In another exemplary embodiment, at least one member selected from $R^1$, $R^2$, $R^3$, $R^4$, $R^5$, $R^6$, $R^7$, $R^8$, $R^9$, $R^{10}$, $R^{11}$, $R^{12}$, and $R^{13}$ is a solid support or is attached to a solid support.

A solid support suitable for use in the present invention is typically substantially insoluble in liquid phases. Solid supports of the current invention are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly (ethylene glycol)), nylon, latex bead, magnetic bead, paramagnetic bead, superparamagnetic bead, starch and the like.

In some embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the compounds of the invention. Useful reactive groups are disclosed above and are equally applicable to the solid support reactive functional groups herein.

A suitable solid phase support can be selected on the basis of desired end use and suitability for various synthetic protocols. For example, where amide bond formation is desirable to attach the compounds of the invention to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (TentaGel™, Rapp Polymere, Tubingen, Germany), polydimethyl-acrylamide resin (available from Milligen/Biosearch, California), or PEGA beads (obtained from Polymer Laboratories).

Preparation of Conjugates

The preparation of dye conjugates using reactive dyes or linkers is well documented, e.g. by R. Haugland, MOLECULAR PROBES HANDBOOK OF FLUORESCENT PROBES AND RESEARCH CHEMICALS, Chapters 1-3 (1996); and Brinkley, BIOCONJUGATE CHEM., 3, 2 (1992). Conjugates typically result from mixing appropriate reactive dyes and the substance to be conjugated in a suitable solvent in which both are soluble. The dyes of the invention are readily soluble in aqueous solutions, facilitating conjugation reactions with most biological materials. For those reactive dyes that are photoactivated, conjugation requires illumination of the reaction mixture to activate the reactive dye.

In-Situ Formation of Conjugates

In one embodiment, compounds and compositions comprising a reactive group passively diffuses into cells, wherein the reactive group reacts with intracellular amines, forming fluorescent conjugates that are well-retained and can be fixed with aldehyde fixatives. Excess unconjugated reagent and by-products passively diffuse to the extracellular medium, where they can be washed away.

The indicator—protein adducts that form in labeled cells can be retained by the cells throughout development, meiosis, and in vivo tracing. The label is inherited by daughter cells after cell division, or cell fusion, and is not transferred to adjacent cells in a population.

Synthesis

A particular aspect of the invention provides a method of making a intracellular ion indicator compound described herein comprising:

contacting a metal ion chelator ($M_c$) with a reporter molecule, such that the reporter molecule covalently binds to the metal ion chelator; and contacting a lipophilic group with a negatively charged substituent present on the reporter molecule, such that the lipophilic group binds covalently to the negatively charged group thereby neutralizing the negatively charged group.

In a more particular embodiment, the negatively charged group is a carboxylate. In another embodiment the reporter molecule is a fluorescent dye. More particularly, the fluorescent dye is a xanthene, such as a 3-aminoxanthene or tatumter thereof.

In a more particular embodiment, the a metal ion chelator ($M_c$) comprises a reactive group when it is contacted with the reporter molecule. More particular still, the reactive group is an aldehyde.

Additional synthetic methods and schemes contemplated as part of the present invention are provided in the Examples section.

Method of Use

The intracellular ion chelating compounds of the invention are useful for any application where it is desirable to complex a metal ion. Selected compounds of the invention may be useful as ionophores, that is, they facilitate the transport of selected target ions across cell membranes. Typically, however the present intracellular ion indicators are useful for detecting, monitoring, quantitating or sequestering of intracellular metal ions that are found in the cytosol or surrogate metal ions not normally found in the cytosol or other cellular compartments. In a preferred embodiment the intracellular ion indicators are well retained in the cytosol or other discrete locations in he cell and when coordinated with an appropriate metal ion emit at a wavelength greater than about 530 nm. Such intracellular metal ions include calcium, magnesium, zinc and potassium as well as any metal ion that can act as a surrogate. Calcium is an important cytosolic metal ion and a preferred method is the use of the present compounds to detect this metal ion using methods well known in the art.

In an alternative embodiment the present compounds are bound to a carrier molecule or solid support such as a bioparticle (e.g. bacterial particles), peptides, antibodies, polymeric particles (e.g. polystyrene beads), receptor binding domains, nucleic acid binding proteins, kinase substrates, phosphatase substrates, and other carrier molecules that are useful for facilitating passive and cell mediated uptake of the present compounds or carrier molecules that are useful for localizing the present compounds such that measurement of the metal ions is indicative of the cellular events in the local environment. Examples of carrier molecules that facilitate passive and cell mediated uptake include antibodies, bioparticles, receptor binding proteins or peptides (binding domain) and the like. Examples of carrier molecules that provide useful information either for localization or because they act as an enzyme substrate include kinase substrates, phosphatase substrates, antibodies, nucleic acid binding proteins, nucleic acids and the like.

In order for a particular indicator of the present invention to be useful for detection purposes, it must exhibit a detectable change in spectral properties upon coordination with an appropriate intracellular metal ion. Preferably the change in spectral properties is a change in fluorescence properties. More preferably, the instant indicators display an intensity increase or decrease in emission energy upon the complexation of the desired target ion.

The present compounds are useful for binding target ions resulting in a complex of the target ion and the present compounds. Therefore, an additional aspect of the invention includes the compound of the invention further comprising a metal ion that is coordinated within the chelate portion of the compound. The metal ion is optionally $Ca^{2+}$, $Zn^{2+}$, $Mg^{2+}$, $Ga^{3+}$, $Tb^{3+}$, $La^{3+}$, $Pb^{2+}$, $Hg^{2+}$, $Cd^{2+}$, $Cu^{2+}$, $Ni^{2+}$, $Co^{2+}$, $Fe^{2+}$, $Mn^{2+}$, $Ba^{2+}$, and $Sr^{2+}$. Preferably the complex comprises physiological relevant cations such as $Ca^{2+}$, $Mg^{2+}$, $Fe^{2+}$ and $Zn^{2+}$. Most preferably, the complex comprises calcium, magnesium, iron, zinc, sodium, potassium or thallium ions.

Accordingly, one aspect of the invention provides a method for binding intracellular metal ions in a sample, comprising:

contacting the sample with a intracellular ion indicator compound, wherein the compound comprises a metal chelating moiety, a reporter molecule and one or more lipophilic groups covalently bonded to the reporter molecule through a linker wherein the lipophilic groups, when present in a live cell, are enzymatically cleaved resulting in one or more negatively charged groups; and incubating the sample and compound for sufficient time to allow the compound to chelate the appropriate intracellular ion whereby the metal ion is bound.

In a more particular embodiment, the method further comprises illuminating the compound with a suitable light source whereby the intracellular ion is detected. In this method the present compounds are incubated with the sample for a sufficient amount of time to allow the compound to be either passively or by cell mediated mechanisms to be taken up by the biological cells. Once inside the cells the labile lipophile groups are enzymatically cleaved resulting in a compound that is well retained in the cytosol or other discrete locations of the cell. The sample is then incubated for a sufficient amount of time to allow the present compounds to chelate the appropriate intracellular metal ion. In this instance, "appropriate metal ion" means an ion that is bound by the chelating moiety present on the intracellular ion indicator. This results in metal ions being bound in the cell.

Another aspect of the invention provides a method for detecting and/or identifying intracellular metal ions in a sample, comprising:

contacting the sample with a intracellular ion indicator compound, wherein the compound comprises a metal chelating moiety, a reporter molecule and one or more lipophilic groups covalently bonded to the reporter molecule through a linker wherein the lipophilic groups, when present in a live cell, are cleaved resulting in one or more negatively charged groups;

incubating the sample for a period of time sufficient for the compound to enter the cell;

cleaving the one or more lipophilic groups; and illuminating the sample with an appropriate wavelength, wherein the intracellular metal ion is identified.

The sample is illuminated with an appropriate wavelength whereby the target ion is detected. In such an assay the target ion can also be quantitated and monitored.

The specific indicator used in an assay or experiment is selected based on the desired affinity for the target ion as determined by the expected concentration range in the sample, the desired spectral properties, and the desired selectivity. Initially, the suitability of a material as an indicator of ion concentration is commonly tested by mixing a constant amount of the indicating reagent with a measured amount of the target ion under the expected experimental conditions.

Preferred indicators display a high selectivity, that is, they show a sufficient rejection of non-target ions. The interference of a non-target ion is tested by a comparable titration of the indicator with that ion. Although preferred target ions for most indicators of the present invention are $Ca^{++}$ any ion that yields a detectable change in absorption wavelengths, emission wavelengths, fluorescence lifetimes or other measurable optical property over the concentration range of interest is potentially measured using one of the indicators of this invention.

The indicator is generally prepared for use as a detection reagent by dissolving the indicator in solution at a concentration that is optimal for detection of the indicator at the expected concentration of the target ion. Modifications that are designed to enhance permeability of the indicator through the membranes of living cells, such as acetoxymethyl esters and acetates, may require the indicator to be predissolved in an organic solvent such as dimethylsulfoxide (DMSO) before addition to a cell suspension, where the indicators then readily enter the cells. Intracellular enzymes cleave the esters to the more polar acids and phenols that are then well retained inside the cells. For applications where permeability of cell-membranes is required, the indicators of the invention are typically substituted by only one fluorophore.

Therefore, a method for binding and detecting target ions in a live cell comprises the following steps:
a) contacting a sample of live cells with a present compound;
b) incubating the sample and the compound for sufficient time to allow the compound to chelate the target metal ion; and,
c) illuminating the sample with an appropriate wavelength to generate a detectable fluorescent signal whereby the target ion is detected in a live cell.

A specific indicator of the present invention is useful for the detection and/or quantification of a desired target ion, when the binding of the target ion in the metal ion-binding moiety of the indicator results in a detectable change in spectral properties. Preferably, the change in spectral properties is a detectable fluorescence response.

The optical response of the indicating reagent is determined by changes in absorbance or fluorescence, preferably fluorescence. If absorbance measurements are used to determine ion concentrations, then it is usually optimal to adjust the optical density of the indicator in the sample over the range of analyte concentration to a value of approximately 0.02 to 2.5 (most preferably 0.1 to 1). For fluorescence measurements, the concentration of the indicator will depend mostly on the sensitivity of the equipment used for its detection.

If the optical response of the indicator will be determined using fluorescence measurements, samples are typically stained with indicator concentrations of $10^{-9}$ M to $10^{-2}$ M. The most useful range of analyte concentration is about one log unit above and below the dissociation constant of the ion-indicator complex. This dissociation constant is determined by titration of the indicator with a known concentration of the target ion, usually over the range of virtually zero concentration to approximately 100 millimolar of the target ion, depending on which ion is to be measured and which indicator is being used. The dissociation constant may be affected by the presence of other ions, particularly ions that have similar ionic radii and charge. It may also be affected by other conditions such as ionic strength, pH, temperature, viscosity, presence of organic solvents and incorporation of the sensor in a membrane or polymeric matrix, or conjugation or binding of the sensor to a protein or other biological molecule. Any or all of these effects need to be taken into account when calibrating an indicator.

The indicator is combined with a sample in a way that will facilitate detection of the target ion concentration in the sample. The sample is generally a representative cell population, fluid or liquid suspension that is known or suspected to contain the target ion. Representative samples include intracellular fluids such as in blood cells, cultured cells, muscle tissue, neurons and the like; extracellular fluids in areas immediately outside of cells; in vesicles; in vascular tissue of plants and animals; in biological fluids such as blood, saliva, and urine; in biological fermentation media; in environmental samples such as water, soil, waste water and sea water; in industrial samples such as pharmaceuticals, foodstuffs and beverages; and in chemical reactors.

In one embodiment of the invention, the sample contains cells, and the indicator is combined with the sample in such a way that the indicator is present within the sample cells. By selection of the appropriate chelating moiety, fluorophore, and the substituents thereon, indicators are prepared that will selectively localize in desired organelles, and provide measurements of the target ion in those organelles. Conjugates of the indicators of the invention with organelle-targeting peptides are used to localize the indicator to the selected organelle, facilitating measurement of target ion presence or concentration within the organelle (as described in U.S. Pat. No. 5,773,227). Alternatively, selection of a lipophilic fluorophore, or a fluorophore having predominantly lipophilic substituents, wherein the lipophilic substituents are not labile, will result in localization in lipophilic environments in the cell, such as cell membranes.

The metal-ion chelating compound is combined with a sample in a way that will facilitate detection of the target ion concentration in the sample. The sample is generally a representative cell population, fluid or liquid suspension that is known or suspected to contain the target ion. Representative samples include intracellular fluids such as in blood cells, cultured cells, muscle tissue, neurons and the like; extracellular fluids in areas immediately outside of cells; in vesicles; in vascular tissue of plants and animals; in biological fluids such as blood, saliva, and urine; in biological fermentation media; in environmental samples such as water, soil, waste water and sea water; in industrial samples such as pharmaceuticals, foodstuffs and beverages; and in chemical reactors. Detection and quantitation of the target ion in a sample can help characterize the identity of an unknown sample, or facilitate quality control of a sample of known origin.

The sample can be a biological fluid such as whole blood, plasma, serum, nasal secretions, sputum, saliva, urine, sweat, transdermal exudates, cerebrospinal fluid, or the like. Biological fluids also include tissue and cell culture medium wherein zinc ions have been secreted into the medium. Alternatively, the sample may be whole organs, tissue or cells from the animal. Examples of sources of such samples include muscle, eye, skin, gonads, lymph nodes, heart, brain, lung, liver, kidney, spleen, thymus, pancreas, solid tumors, macrophages, mammary glands, mesothelium, and the like. Cells include without limitation prokaryotic cells and eukaryotic cells that include primary cultures and immortalized cell lines. Eukaryotic cells include without limitation ovary cells, epithelial cells, circulating immune cells, β cells, hepatocytes, and neurons. Calcium and zinc ions have been determined to play a role in many mammalian, if not all, organs and cell types such that there is no intended limitation on the sample for the present invention.

The end user will determine the choice of the sample and the way in which the sample is prepared. For example the sample may include a mixture of cells, or prepared for HTS, or for imaging by flow cytometry. The sample includes, without limitation, any biological derived material that is thought to contain target ions, preferably calcium. Alternatively, samples also include material that target ions have been added to determine the effect the ions have on predetermined biological parameters.

A preferred embodiment of the present invention involves long wavelength intracellular ion indicator. The long wavelength indicators avoid cellular autofluorescence and interference from other agents such as drugs which have been introduced to cell. The long wavelength intracellular ion indicators also allow for unique detection signals in multiplexing applications, such as with GFP's or other indicators. Accordingly, one embodiment of the present invention involves detection of multiple analytes or metal ions simultaneously via introduction of the compositions described herein and different indicator comprising a reporter molecule or dye.

Quantification of target ion levels in samples is typically accomplished using the indicators of the present invention by methods known in the art. For example, the ratiometric measurement of ion concentration provides accurate measurement of ion concentrations by the treatment of the fluorescence data as the ratio of excitation or fluorescence intensities at two wavelengths, rather than the absolute intensity at a single wavelength. Using the ratio method, a number of variables that may perturb the ion concentration measurements are eliminated. In particular, ion-dependent factors that affect the signal intensity, such as nonuniform intracellular dye concentrations, probe leakage, dye bleaching and cell thickness, are canceled in the ratio measurements, since these parameters have a similar effect on intensities at both wavelengths. While the ratio method can be used to determine concentrations using observation of either the excitation spectra of the indicator, the emission spectra of the indicator, or both, in the case of the indicators of the present invention, the shift in excitation energy upon binding metal ions makes observation of the excitation spectrum a more useful technique. In either case, to achieve maximal utility, the indicator must be calibrated (to compensate for variance in the dissociation constant of the indicator due to ionic strength, viscosity, or other conditions within the sample). To calibrate the indicator, ionophores such as A-23187, gramicidin, valinomycin, or ionomycin are used. Non-ratiometric analysis can also be accomplished by calibration with a second fluorescent dye present in the sample.

The optical response of the indicator to the ion can be detected by various means that include measuring absorbance or fluorescence changes with an instrument, visually, or by use of a fluorescence sensing device. Several examples of fluorescence sensing devices are known, such as fluorometers, fluorescence microscopes, laser scanners, flow cytometers, and microfluidic devices, as well as by cameras and other imaging equipment.

Kits of the Invention

Due to the advantageous properties and the simplicity of use of the present intracellular ion indicators, they are particularly useful in the formulation of a kit for the complexing, detection, quantification or monitoring of selected target ions, such as calcium, comprising one or more compounds or compositions of the invention in any of the embodiments described above (optionally in a stock solution), instructions for the use of the compound to complex or detect a desired target ion, and optionally comprising additional components.

A particular kit for binding an intracellular metal ion in a sample, comprises:
a compound of formula:

wherein,
$G_L$ is a lipophilic group:
DYE is a fluorescent dye; and
$M_c$ is a metal chelating moiety; and
one or more components selected from the group consisting of a calibration standard of an intracellular metal ion, an ionophore, a fluorescent standard, an aqueous buffer solution and an organic solvent.

A kit of the present invention for binding a target metal ion in a sample may comprise a compound as described herein and instructions for use thereof. The kit may further comprise one or more components selected from the group consisting of a calibration standard of a metal ion, an ionophore, a fluorescent standard, an aqueous buffer solution, control cells and an organic solvent.

The additional kit components may be selected from, without limitation, calibration standards of a target ion, ionophores, fluorescence standards, aqueous buffers, control cells and organic solvents. The additional kit components are present as pure compositions, or as aqueous solutions that incorporate one or more additional kit components. Any or all of the kit components optionally further comprise buffers.

Illumination:

In a typical detection method, at any time after or during binding of the compounds of the present invention with the target metal ion, the sample is visualized whereby the compound is detected. Visualization can comprise different methods and is dependent on the reporter molecule that is covalently attached to the metal ion chelator. When the reporter molecule is a dye label, visualization typically comprises illumination with a wavelength of light capable of exciting the dye to produce a detectable optical response, as defined above, and observed with a means for detecting the optical response. Equipment that is useful for illuminating the dye compounds of the invention includes, but is not limited to, hand-held ultraviolet lamps, mercury arc lamps, xenon lamps, lasers and laser diodes. These illumination sources are optionally integrated into laser scanners, fluorescence-based microplate readers, standard or minifluorometers, flow cytometers or chromatographic detectors. The degree and/or location of binding/chelation, compared with a standard or expected response, indicates whether and to what degree the sample possesses a given characteristic, i.e., cell processes/activity.

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, fluorescence-based microplate readers, or by a means for amplifying the signal such as photomultiplier tubes.

Thus, it is contemplated by the present invention that a wide variety of instrumentation may be used to detect target metal ions.

As described above, while a wide variety of methods of detection are used with the present invention, a preferred method includes the use of fluorescence. Fluorescence from the compound binding to the target metal ion can be visualized with a variety of imaging techniques, including ordinary light or fluorescence microscopy.

The examples below are given so as to illustrate the practice of this invention. They are not intended to limit or define the entire scope of this invention.

EXAMPLES

The present invention further provides compounds, intermediates, methods of synthesis and methods of use involving any of the following example compounds.

The starting materials for the synthesis of calcium ion indicators were described in: Martin, V. V.; Beierlein, M.; Morgan, J. L.; Rothe, A.; Gee, K. R. Cell Calcium 2004, 36, 509, and in: Beierlein, M.; Gee, K. R.; Martin, V. V.; Regehr, W. G. *J. Neurophysiol.* 2004, 92(1), 591. Preparation of the starting materials for sodium indicators were published in: Martin, V. V.; Rothe, A.; Diwu, Z.; Gee, K. R. *Bioorg. Med. Chem. Lett.* 2004, 14, 5313, and in Martin, V. V.; Rothe, A.; Gee, K. R. *Bioorg. Med. Chem. Lett.* 2005, 15, 1855.

Example 1

Synthesis of a cell-permeable calcium ion indicator 146 having tetrakis(2-carboxyethyl)rhodamine fluorophore [synthesis of this fluorophore was adopted from: Bandichhor, R.; Petrescu, A. D.; Vespa, A.; Kier, A. B.; Schroeder, F.; Burgess, K. *Bioconjugate Chem.* 2006 17(5), 1219] with extra four carboxylic groups protected as AM esters. (Scheme 100).

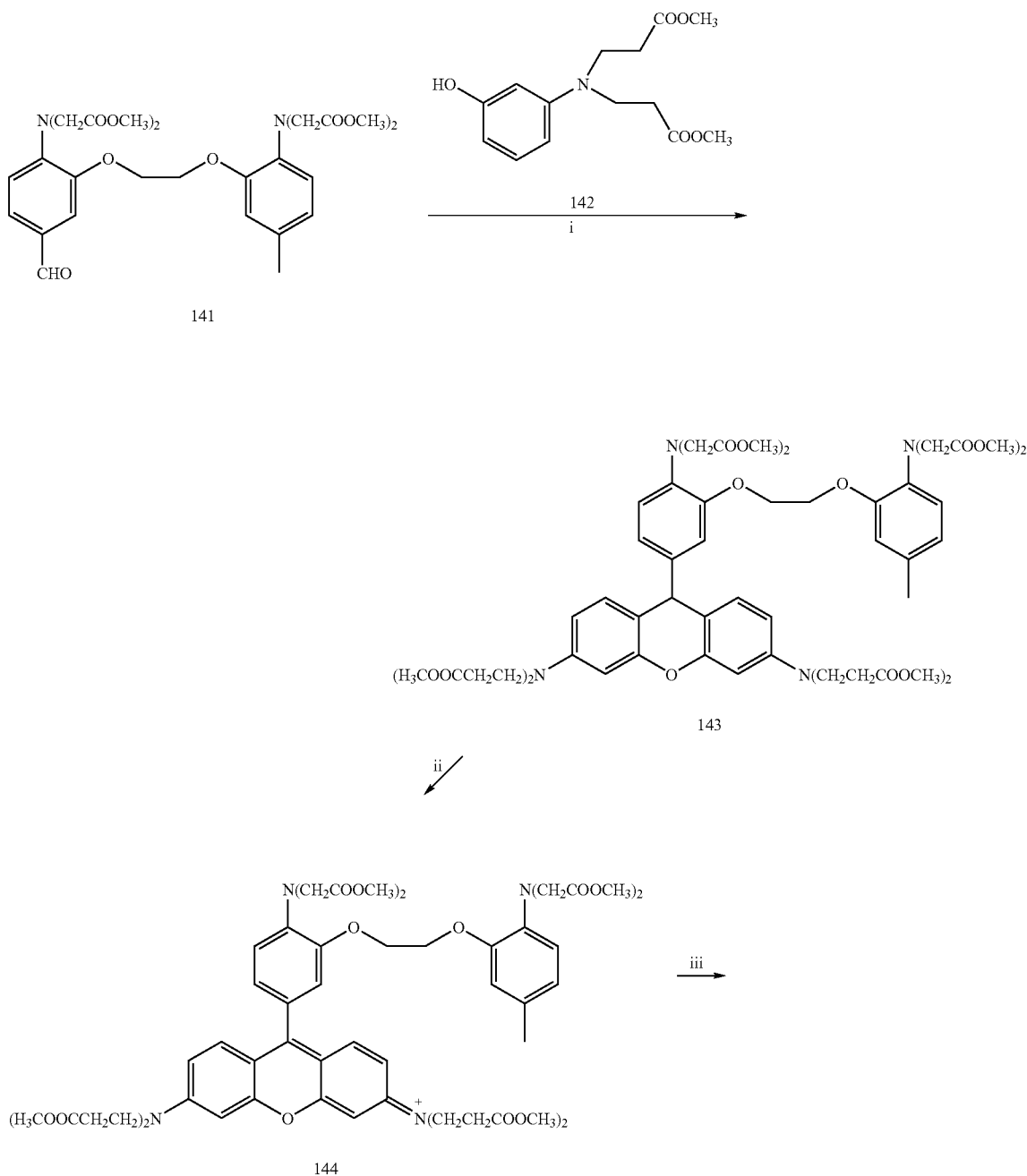

-continued

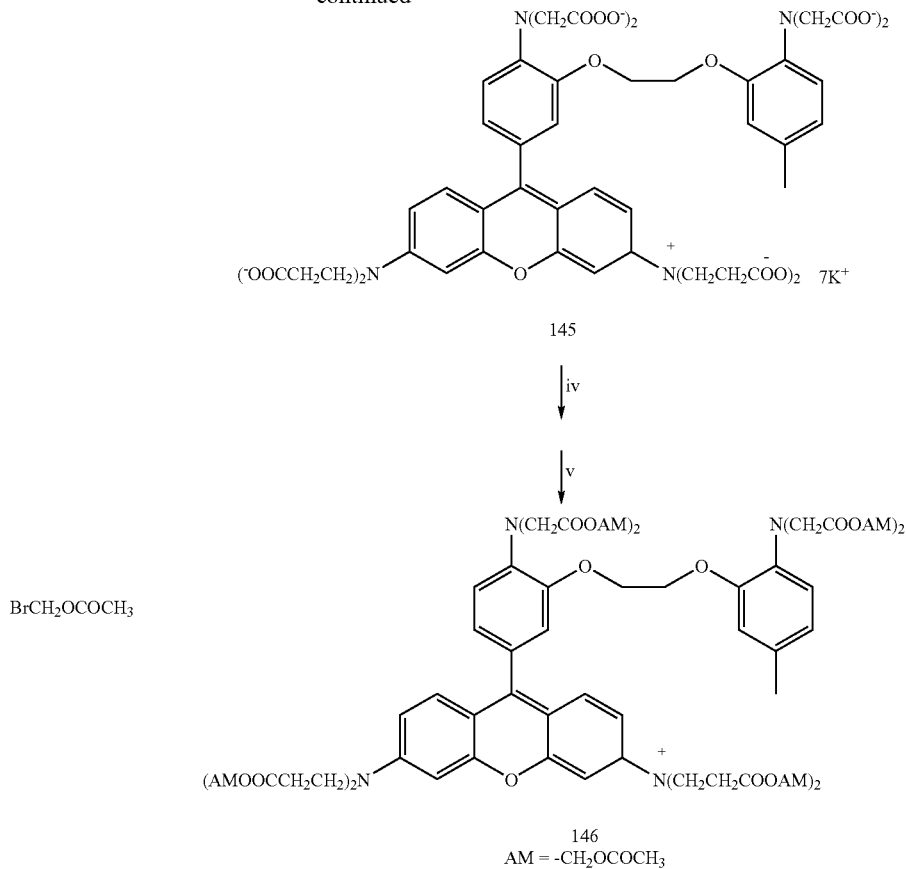

i. EtCOOH, R—SO₃H; ii. Cloranil, CHCl₃/MeOH; iii. KOH/H₂O; iv. t-Bu₄NHSO₄; v. BrCH₂OCOCH₃/DIEA, DMF.

Compound 143. The mixture of the aldehyde 141 (1.120 g, 2 mmol), diester 142 (1.348 g, 4.8 mmol) and 10-camphorsulfonic acid (40 mg; catalyst) in EtCOOH (40 mL) was stirred at 70° C. for 48 h. It was cooled to rt, poured into a mixture of 3N NaOAc (500 mL) and sat. NaHCO₃ 200 mL), and extracted with CHCl₃ (200 mL+8×50 mL). The extract was washed with sat NaCl (300 mL), dried over MgSO₄ to give the compound 143 (2.20 g, ~100%), which was used in the next step without purification.

Octamethyl ester 144. A crude dihydro compound 143 (~2 mmol) was stirred with chloranil (0.984 g, 4 mmol) in CHCl₃/MeOH (1:1) (60 mL) for 5 h. The mixture was filtered, evaporated. The residue was re-dissolved in CHCl₃ (25 mL), loaded onto silica gel column (6×50 cm bed, packed in 3% MeOH and 1% AcOH in CHCl₃) and chromatographed in 3% to 10% gradient MeOH in CHCl₃ and 1% AcOH. The fractions, containing product were evaporated, co-evaporated with toluene (50 mL), dissolved in CHCl₃ (250 mL), allowed to stand for 3 h, filtered from silicates and evaporated to give the compound 144 (0.647 g, 28%) as a dark red oil.

Heptapotassium salt 145. To a stirred solution of the compound 144 (55 mg, 0.02 mmol) in MeOH (2 mL) was added 1 N KOH (0.5 mL, 0.5 mmol). The mixture was stirred for 16 h, diluted with H₂O (5 ml) and 0.2 N HCl was added to pH 9.5.

The solution was evaporated, the residue was re-dissolved in H₂O (3 mL) and loaded onto Sephadex LH-20 column (2.6× 95 cm bed, packed with H₂O) and eluted with H₂O. Combined fractions containing the product were evaporated to ~2 mL volume and lyophilized to give the compound 145 (8 mg, 43%) as hygroscopic dark red flakes.

Octo-AM ester 146. To a solution of the salt 145 (2.5 mg, 0.002 mmol) in MeOH (2 mL) a dry tetrabutylammonium hydrosulfate (17 mg, 0.05 mmol) was added. The mixture was stirred for 5 min, and evaporated. The residue was dissolved in DMF (0.2 mL); DIEA (70 μL, 0.4 mmol) was added followed by bromomethyl acetate (20 μL, 0.2 mmol). The resulted solution was stirred for 16 h and diluted with CHCl₃ (50 mL). Chloroform solution was washed with 1% AcOH (3×30 mL), H₂O (2×30 mL), brine (50 mL), filtered through paper and evaporated to give the compound 146 (3.0 mg, 91%) as a dark red oil.

Example 2

Synthesis of the compounds 153 and 154, reduced-leakage sodium ion indicators for extracellular and intracellular applications (scheme 101)

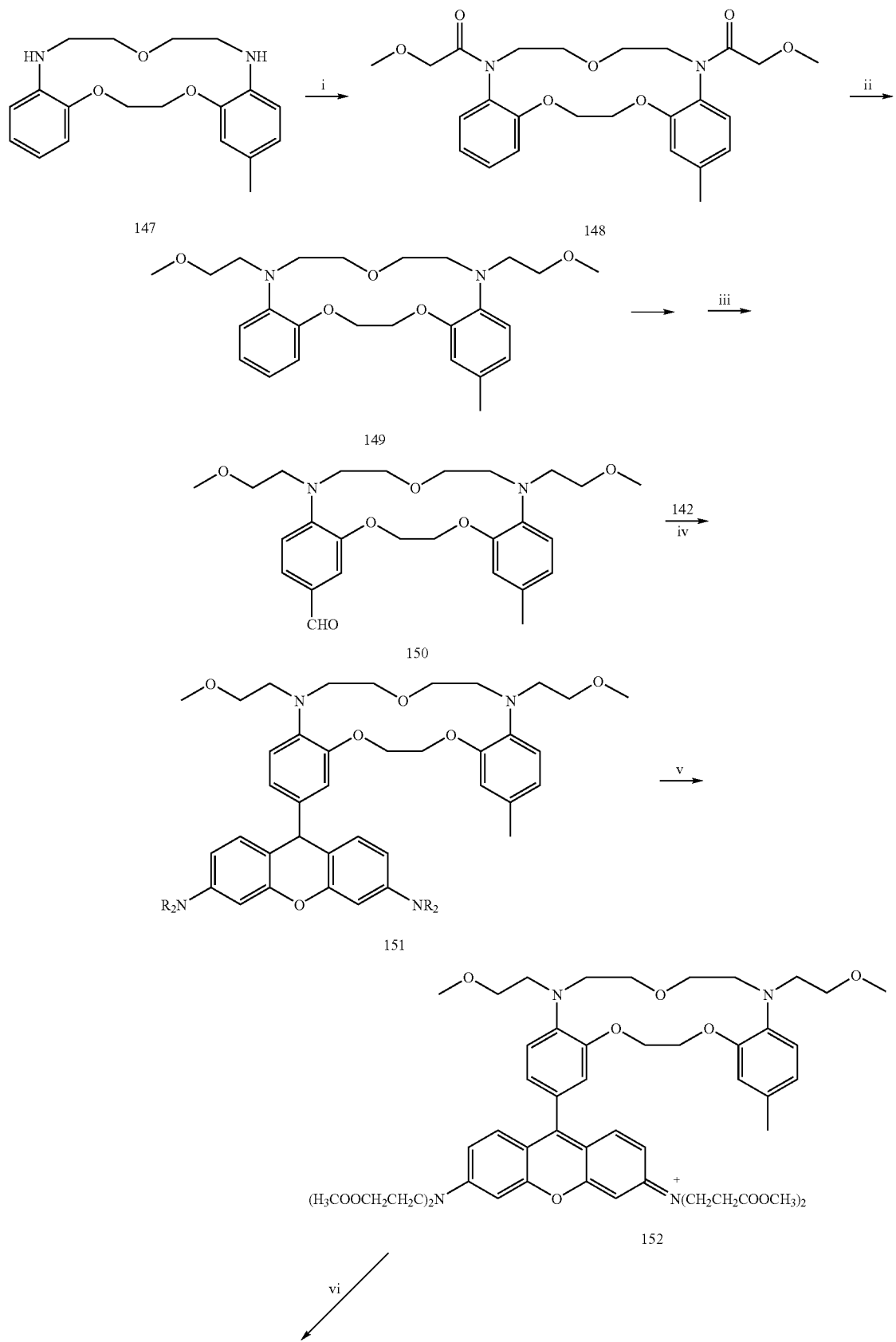

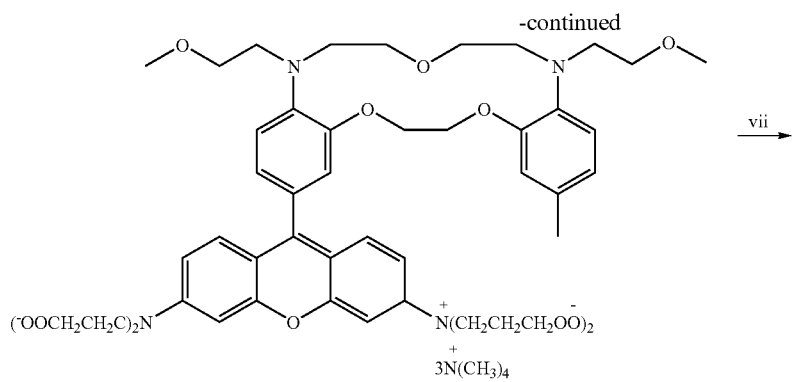

153

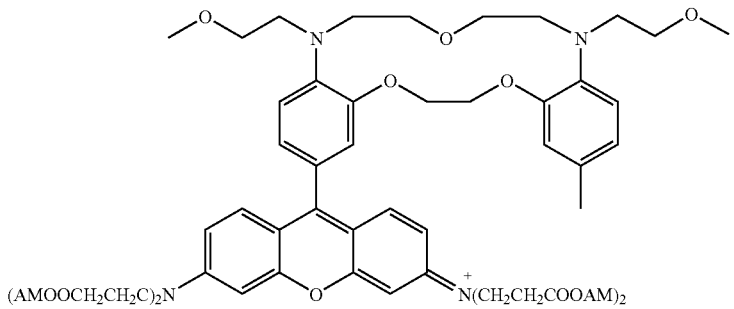

154 i. Methoxyacetyl chloride/DIEA; ii. B₂H₆/THF; iii. POCl₃/DMF;
iv. EtCOOH, R—SO₃H;
v. Cloranil, CHCl₃/MeOH; vi. NMe₄OH/H₂O;
vii. BrCH₂OCOCH₃/DIEA, DMF.

Compound 148. To a stirred solution of the diamine 147 (1.690 g, 5 mmol) in THF (20 mL) and DIEA (2.6 mL), methoxyacetyl chloride (1.1 mL, 12 mmol) in THF (20 mL) was added dropwise while cooling on the ice bath. The mixture was for 15 min, then cooling was removed and the stirring was continued for 2 h. The DIEA salt was filtered off; filtrate was evaporated, the residue was dissolved in EtOAc (200 mL), washed with 1% HCl (2×100 mL), H₂O (100 mL), brine (100 mL), filtered through paper filter and evaporated to give the compound 148 (1.71 g, 00) as an off-white foamy solid.

Compound 149. Bis-acyl derivative 148 (1.70 g, 3.73 mmol) and B₂H₆-THF complex (1 N in THF; 37 mL, 37 mmol) in THF (50 mL) were refluxed overnight, cooled to rt and carefully decomposed with methanol (100 mL total) [warning: controlled addition required; violent reaction!]. The mixture was again heated to reflux, stirred for more 1 h, evaporated, and co-evaporated with MeOH (3×50 mL) to give the compound 149 (1.585 g, 99%) as a yellowish viscous oil.

Aldehyde 150. A mixture of the compound 149 (1.580 g, 3.69 mmol) and (chloromethylene)dimethylammonium chloride (2.36 g, 18.46 mmol) in DMF (20 mL) was stirred at 50° C. for 48 h, cooled to rt and poured into ice/sat. NaHCO₃ (1:1, 200 mL). The mixture was extracted with CHCl₃ (10×50 mL), the extract was washed with brine (100 mL), dried over MgSO₄, and evaporated. The residue was purified by column chromatography on a silica gel column (packed in 3% MeOH in CHCl₃) using 3% MeOH in CHCl₃ as eluant to give the aldehyde 150 (0.425 g, 24%) as a yellowish oil.

Compound 151. The mixture of the aldehyde 150 (0.420 g, 0.84 mmol), diester 142 (0.566 g, 2.02 mmol) and 10-camphorsulfonic acid (18 mg; catalyst) in EtCOOH (17 mL) was stirred at 70° C. for 24 h. It was cooled to rt, poured into a mixture of 3N NaOAc (200 mL) and 1 N NaOH (5 mL), and extracted with CHCl₃ (100 mL+6×30 mL). The extract was washed with sat NaCl (300 mL), dried over MgSO₄ to give the compound 151 (0.8 g, ~100%), which was used in the next step without purification.

Tetramethyl ester 152. A crude dihydro compound 151 (~0.8 mmol) was stirred with chloranil (0.590 g, 4 mmol) in CHCl₃/MeOH (1:1) (3 mL) for 5 h. The mixture was filtered, evaporated. The residue was re-dissolved in CHCl₃ (25 mL), loaded onto silica gel column (3×50 cm bed, packed in 5% MeOH and 1% AcOH in CHCl₃) and chromatographed in 5% to 10% gradient MeOH in CHCl₃ and 1% AcOH. The fractions, containing product were evaporated, co-evaporated with toluene (50 mL), dissolved in CHCl₃ (150 mL), allowed to stand for 3 h, filtered from silicates and evaporated to give the compound 152 (0.147 g, 18%) as a dark red oil.

Tetra (tetramethylammonium) salt 153. To a stirred solution of the compound 152 (21 mg, 0.02 mmol) in MeOH (1 mL) and dioxane (1 mL) was added tetramethylammonium hydroxide (~2.8 N in water; 0.15 mL, 0.4 mmol). The mixture was stirred for 20 h and evaporated; the residue was re-dissolved in H₂O (3 mL) and loaded onto Sephadex LH-20 column (2.6×95 cm bed, packed with H₂O) and eluted with H₂O. Combined fractions containing the product were evaporated to ~2 mL volume and lyophilized to give the compound 153 (22 mg, 95%) as hygroscopic dark red flakes.

Tetra-AM ester 154. To a solution of the salt 153 (11 mg, 0.01 mmol) in DMF (0.1 mL); DIEA (174 µL, 1 mmol) was added followed by bromomethyl acetate (23 µL, 0.25 mmol).

The resulted solution was stirred for 4 h and diluted with CHCl₃ (50 mL). Chloroform solution was washed with 1% AcOH (3×30 mL), H₂O (2×30 mL), dried over MgSO₄, filtered and evaporated to give the compound 154 (10 mg, 79%) as a dark red hygroscopic solid.

Example 3

Synthesis of the compounds 156 and 157: reduced-leakage na⁺ indicators—for extracellular and intracellular environments Scheme 102

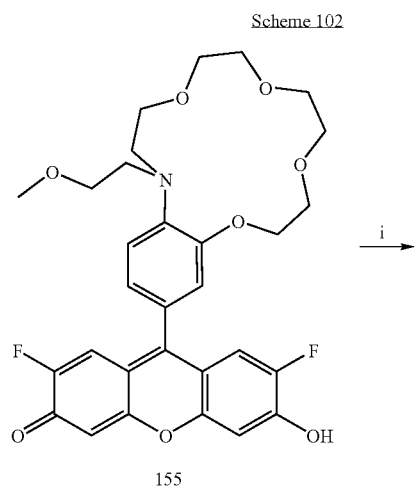

155

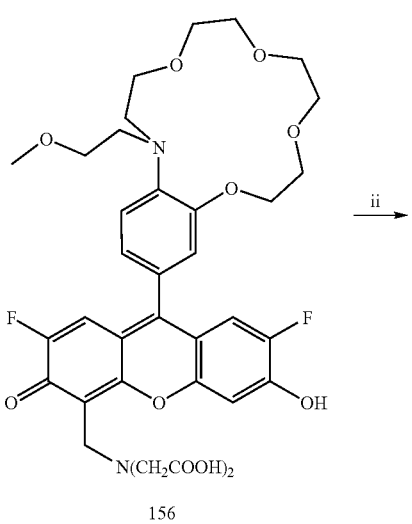

156

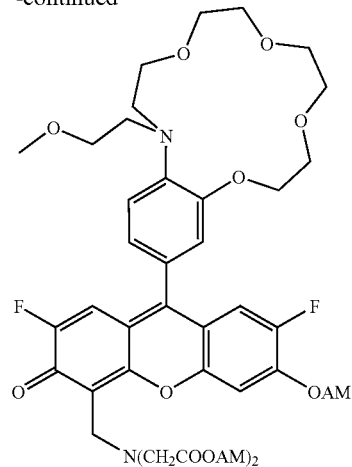

157 i. Iminodiacetic acid/CH₂O/KOH; ii. BrCH₂OCOCH₃/DIEA, DMF.

Dicarboxylic acid 156. To a stirred solution of the compound 155 (114 mg, 0.2 mmol) in MeOH (2 mL), is added iminodiacetic acid (33 mg, 0.25 mmol) in 6N KOH (1 mL). Diluted hydrochloric acid (0.2 N) is added to pH 9.5 and the solution of 37% formaldehyde (0.8 mL, 1 mmol) in MeOH (2 mL) is introduced. The mixture is stirred for 10 h, and evaporated. The residue is dissolved in water (100 mL), washed with CHCl₃ (50 mL), acidified with 0.2 N HCl to pH 4, and extracted with CHCl₃ (10×20 mL). Extract is dried over MdSO₄, and evaporated. The residue is loaded onto chromatography column (2.5×40 cm bed, packed with CHCl₃) and eluted with 3% to 10% MeOH gradient in CHCl₃ to give the compound 156.

Tris-AM derivative 157. To a solution of the dicarboxylic acid 156 (36 mg, 0.05 mmol) in DMF (2 mL); DIEA (175 µL, 1.0 mmol) is added followed by bromomethyl acetate (50 µL, 0.53 mmol). The resulted solution is stirred for 6 h and diluted with CHCl₃ (100 mL). Chloroform solution was washed with H₂O (5×50 mL), brine (50 mL), filtered through paper filter and evaporated to give the compound 157.

Example 4

Figure 1A:
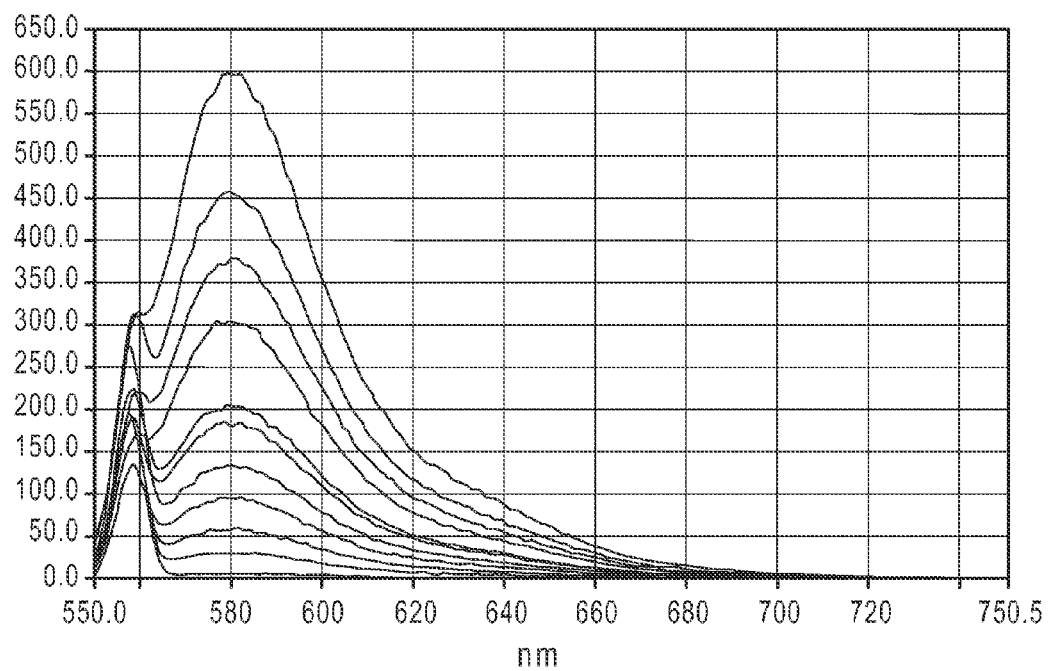
FIG. 1A shows changes in emission spectrum upon increase of [$Ca^{2+}$] concentration and FIG. 1B shows determination of the binding constant
Figure 1B:
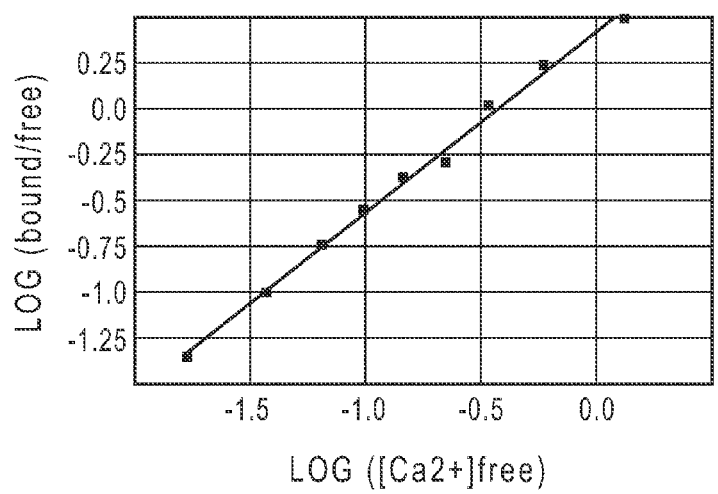

Spectroscopic study of the calcium binding to compound 145 ($\lambda_{ex}$=555 nm, $\lambda_{em}$=580 nm; $K_d$=380 nmol)
a) Changes in emission spectrum upon increase of [Ca²⁺] concentration
b) Determination of the binding constant. Results are shown in FIG. 1.

Example 5

Imaging of cellular localization of a) conventional red Ca indicator Rhod-2 (Mitochondrial Localization), b) Compound 146, and c) Cytosolic Indicator Fluo-4
Results are shown in FIG. 2.

Example 105

Determination of intracellular calcium with Compound 146 in a Multiwell Plate

CHOM1 cells were plated in poly d lysine coated 96 well plates at a density of 35,000 cells per well on the morning of the experiment and allowed to settle for four hours in complete medium. The medium was aspirated from the cells and 100 uL HBSS buffer was added. The HBSS buffer was prepared by adding 20 mM HEPES to calcium and magnesium containing HBSS buffer (IVGN catalogue number 14025) and pH set to 7.4 with NaOH. This solution was filter sterilized and stored at 4 C. Following incubation the HBSS buffer was aspirated and replace with 100 uL Loading Buffer. The Loading Buffer (10 ml for one 96 well plate) was prepared as follows: To a 15 mL tube, add in order 100 uL Powerload (IVGN catalogue number F10017); 10 uL of 10 mM dye in DMSO Mix gently by swirling (Stock preparations of Compound 146 were prepared at 10 mM in anhydrous DMSO and aliquots stored frozen at −20 C) and 10 mL Probenecid containing Assay Buffer. The assay buffer was prepared by diluting water soluble probenecid stock 1:100 in HBSS buffer on the day of use. The water soluble probenecid (Invitrogen catalogue number P36400) was prepared at 100× by adding 1 mL deionized water to a 77 mg vial of water soluble probenecid. Unused portions were stored frozen at −20 C.

Figure 3A:
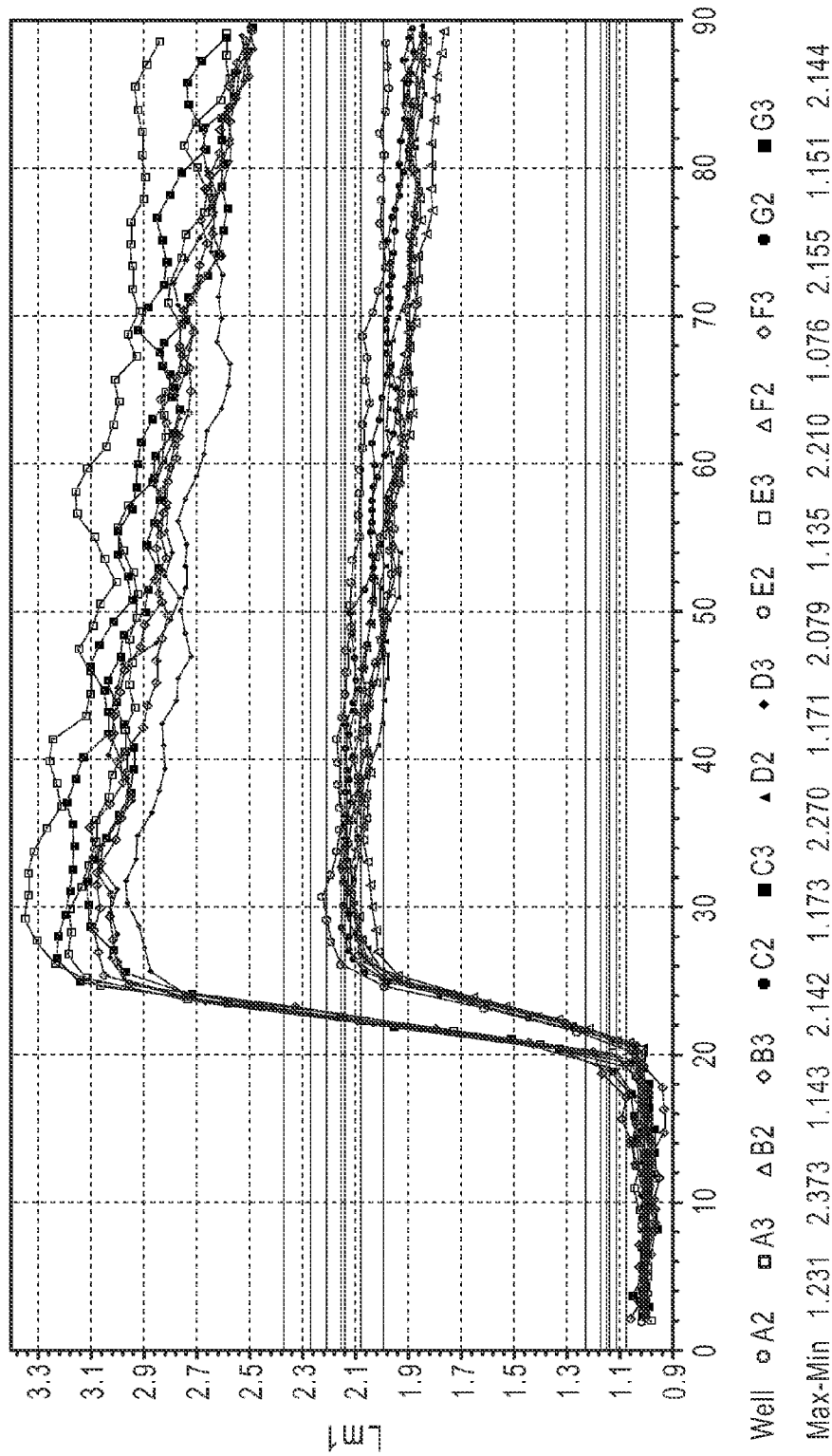
FIG. 3 shows detection of intracellular calcium after a (FIG. 3A) 1 uM final carbachol stimulation and (FIG. 3B) a dose-response study of carbachol in CHOM1 cells loaded as above with 10 and 20 uM Rhod-2 vs 10 and 20 uM Compound 146.
Figure 3B:
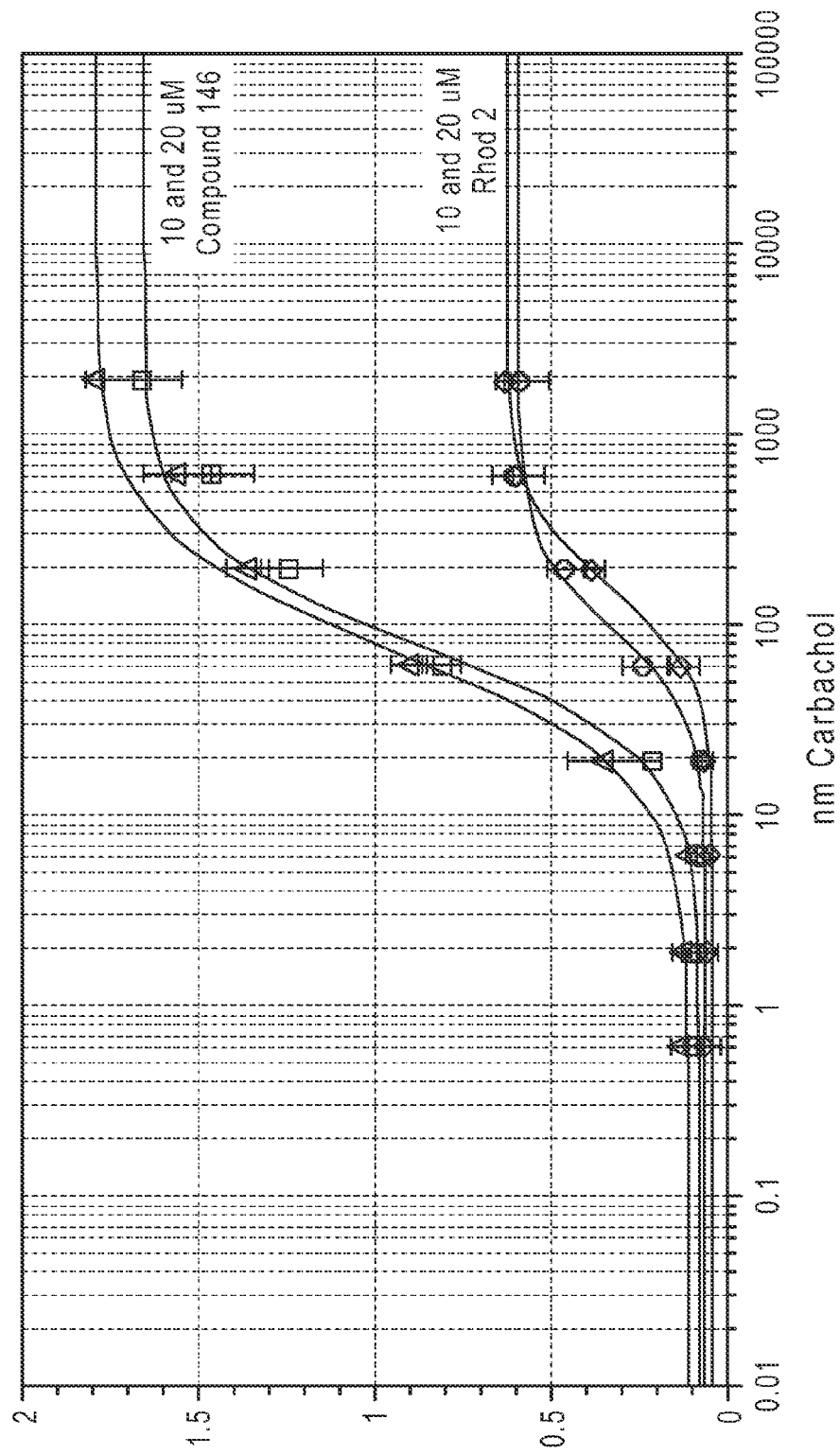

Following incubation with Loading Buffer the cells are placed 37 C for 60 minutes room atmosphere, not 5% CO2 incubator. The loading buffer was aspirated and replaced with 100 uL Probenecid containing Assay Buffer. The Loading buffer was then replaced with 100 uL Probenecid containing Assay Buffer The cells are imaged using a standard microplate reader (FlexStationII384, Molecular devices, Sunnyvale Calif.) set to 550 nanometers (nm) excitation, 600 nm emission with excitation cutoff at 590 nm. Readings are taken every 2 seconds for 20 seconds and then 25 uL of carbachol containing stimulus is added to the microwells for a 1:5 dilution. A 1 uM final carbachol stimulation results in a signal such as seen in FIG. 3A.

A dose-response study of carbachol in CHOM1 cells loaded as above with 10 and 20 uM Rhod-2 vs 10 and 20 uM Compound 146 is shown in FIG. 2.

The invention claimed is:

1. An intracellular ion indicator compound, wherein the compound comprises a metal chelating moiety ($M_c$), a reporter molecule and two or more lipophilic groups (GO covalently bonded through a linker to the reporter molecule, wherein the lipophilic groups, when present in a live cell, are cleaved resulting in two or more negatively charged groups.

2. The compound of claim 1, wherein the metal chelating moiety ($M_c$) is covalently bonded through a PET linker to the reporter molecule.

3. The compound of claim 1, wherein the reporter molecule is a fluorescent dye.

4. The compound of claim 1, wherein the lipophilic groups comprise an ester.

5. The compound of claim 4, wherein the two or more negatively charged groups are carboxylate groups.

6. The compound of claim 1, wherein the lipophilic groups are selected from the group consisting of $C_1$-$C_6$ carboxyalkyl, $-(CH_2)_{1-6}COOCR^{15}{}_2OC(=O)(CH_2)_{0-4}CH_3$, and alpha-acyloxyalkyl; wherein $R^{15}$ is H, alkyl or substituted alkyl.

7. The compound of claim 1, wherein the lipophilic groups are:
$-CH_2CH_2COOCH_2OC(=O)CH_3$.

8. The compound of claim 3, wherein the fluorescent dye comprises at least three lipophilic groups.

9. The compound according to claim 3, wherein the compound has the formula:

$(G_L)_v$-L-DYE-$M_c$ wherein,
L is a linker;
$G_L$ is a lipophilic group;
DYE is a fluorescent dye;
$M_c$ is a metal chelating moiety; and
v is 2, 3, 4, or 5.

10. The compound of claim 9, wherein DYE is a 3-aminoxanthene or tautomer thereof.

11. The compound of claim 1, wherein $M_c$ is a metal ion chelator capable of binding calcium, magnesium, zinc, iron, thallium, sodium or potassium.

12. The compound of claim 1, wherein $M_c$ comprises BAPTA or BAPTA derivative, a crown ether moiety, a cryptan, APTRA, FluoZin-1, 2 or 3 or a phenanthroline.

13. The compound of claim 1, wherein $M_c$ has the structure:

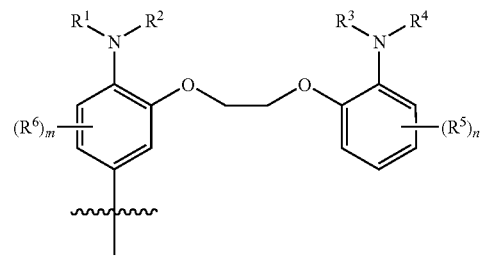

wherein,
$R^1$, $R^2$, $R^3$ and $R^4$ are each independently selected from the group consisting of carbonyl, substituted carbonyl, carboxyl, alkyl, substituted alkyl, and -L-$(G_L)_w$; or
$R^2$ and $R^4$ are bound together by: $-(CH_2CH_2-O)_t-CH_2CH_2-$, wherein t is 1 or 2;
$R^5$ and $R^6$ are each independently selected from the group consisting of -L-$(G_L)_w$, alkyl, substituted alkyl, carbonyl, substituted carbonyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;
L is a linker;
$G_L$ is a lipophilic group;
w is 1 or 2; and
m and n are each independently 0, 1, 2, or 3.

14. The compound of claim 13, wherein n is 1 and $R^5$ is $-CH_3$.

15. The compound of claim 13, wherein $R^2$ and $R^4$ are bound together by:
$-CH_2CH_2-O-CH_2CH_2-$.

16. The compound of claim 13, wherein $R^1$, $R^2$, $R^3$ and $R^4$ are -L-$(G_L)_w$.

17. The compound of claim 13, wherein L is a single covalent bond, or a covalent linkage that is linear or branched, cyclic or heterocyclic, saturated or unsaturated, having 1-30 nonhydrogen atoms selected from the group consisting of C, N, P, 0 and S; and are composed of any combination of ether, thioether, amine, ester, carboxamide, sulfonamide, hydrazide bonds and aromatic or heteroaromatic bonds.

18. The compound of claim 13, wherein L is -oxo-, alkoxy, -amino-, or -substituted amino-.

19. The compound of claim 1, wherein $M_c$ has the structure:

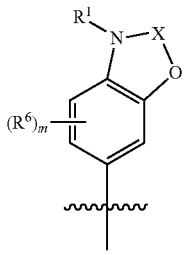

wherein,
X is —(CH$_2$CH$_2$—O)$_y$—CH$_2$CH$_2$—, wherein y is 1, 2, 3, 4, or 5;
$R^1$ is H, alkyl, substituted alkyl, carbonyl, or substituted carbonyl;
$R^6$ is selected from the group consisting of -L-(G$_L$)$_w$, alkyl, substituted alkyl, carbonyl, substituted carbonyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO$_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;
L is a linker;
w is 1 or 2;
$G_L$ is a lipophilic group; and
m is 0, 1, 2, or 3.

20. The compound of claim 3, wherein the fluorescent dye comprises a 3-aminoxanthene or a tautomer thereof.

21. The compound of claim 3, wherein the fluorescent dye comprises a 3,6-diaminoxanthene or a tautomer thereof.

22. The compound of claim 3, wherein the fluorescent dye has the structure:

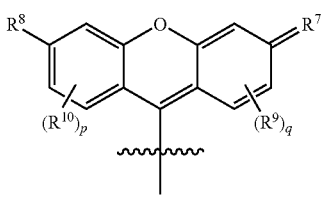

wherein,
$R^9$ and $R^{10}$ are each independently selected from the group consisting of alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO$_3$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, substituted heterocyclyl, and -L-(G$_L$)$_w$;
$R^7$ is =O or =N(R$^{11}$)$_2$, wherein R$^{11}$ is H, alkyl, (G$_L$)$_w$, substituted alkyl, carbonyl, or substituted carbonyl;
$R^8$ is hydroxyl, —OR$_{13}$ or —N(R$^{12}$)$_2$ wherein R$^{12}$ and R$^{13}$ are independently H, alkyl, (G$_L$)$_w$, substituted alkyl, carbonyl, or substituted carbonyl;
or one or both of $R^8$ and (R$^{10}$)$_p$ and $R^7$ and (R$^9$)$_q$ are taken together to form a fused aryl or heteroaryl group;
L is a linker;
$G_L$ is a lipophilic group;
w is 1 or 2; and
p and q are each independently 0, 1 or 2;
wherein the dye comprises at least two $G_L$ groups.

23. The compound of claim 22, wherein $R^7$ is =O, $R^8$ is hydroxyl, p+q=1 and $R^9$ or $R^{10}$ is -L-(G$_L$)$_w$.

24. The compound of claim 22, wherein $R^9$ is -L-(G$_L$)$_w$ and q is 1.

25. The compound of claim 22, wherein L is a single covalent bond, or a covalent linkage that is linear or branched, cyclic or heterocyclic, saturated or unsaturated, having 1-30 nonhydrogen atoms selected from the group consisting of C, N, P, O and S; and are composed of any combination of ether, thioether, amine, ester, carboxamide, sulfonamide, hydrazide bonds and aromatic or heteroaromatic bonds.

26. The compound of claim 22, wherein L is alkyl, substituted alkyl, -oxo-, alkoxy, -amino-, or -substituted amino-.

27. The compound of claim 22, wherein $R^7$ is =N$^+$(G$_L$)$_2$ and $R^8$ is —OG$_L$.

28. The compound of claim 22, werein $R^7$ is =N$^+$(G$_L$)$_2$ and $R^8$ is —N(G$_L$)$_2$.

29. The compound of claim 28, wherein $G_L$ is —(CH$_2$)$_{1-6}$COOCR$^{15}$$_2$OC(=O)(CH$_2$)$_{0-4}$CH$_3$ wherein R$^{15}$ is H, alkyl or substituted alkyl.

30. The compound of claim 28, wherein $G_L$ is —CH$_2$CH$_2$COOCH$_2$OC(=O)CH$_3$.

31. The compound of claim 3, wherein the fluorescent dye has the structure:

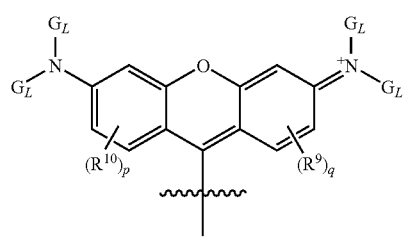

$R^9$ and $R^{10}$ are each independently selected from the group consisting of alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO$_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, substituted heterocyclyl and -L-(G$_L$)$_w$;
L is a linker;
$G_L$ is a lipophilic group;
w is 1 or 2; and
p and q are each independently 0, 1 or 2.

32. The compound of claim 31, wherein $G_L$ comprises an ester.

33. The compound of claim 31, wherein $G_L$ is selected from the group consisting of $C_1$-$C_6$ carboxyalkyl, —$(CH_2)_{1-6}$COOCR$^{15}_2$OC(=O)(CH$_2$)$_{0-4}$CH$_3$, and alpha-acyloxyalkyl; wherein R$^{15}$ is H, alkyl or substituted alkyl.

34. The compound of claim 31, wherein the $G_L$ is: —CH$_2$CH$_2$COOCH$_2$OC(=O)CH$_3$.

35. A method for binding a intracellular metal ion in a sample, comprising:
   contacting the sample with a intracellular ion indicator compound, wherein the compound comprises a metal chelating moiety, a reporter molecule and one or more lipophilic groups covalently bonded to the reporter molecule through a linker wherein the lipophilic groups, when present in a live cell, are cleaved resulting in one or more negatively charged groups; and
   incubating the sample and compound for sufficient time to allow the compound to chelate the intracellular ion whereby the intracellular ion is bound.

36. The method of claim 35, wherein the method further comprises illuminating the compound with a suitable light source whereby the calcium ion is detected.

37. The method of claim 35, wherein the sample comprises cells.

38. The method of claim 37, wherein the incubating step comprises incubating the sample and compound for sufficient time to allow the compound to enter a cell.

39. The method of claim 38, wherein the intracellular ion is bound in the cell.

40. A method for identifying intracellular intracellular metal ions in a sample, comprising:
   contacting the sample with a intracellular ion indicator compound, wherein the compound comprises a metal chelating moiety, a reporter molecule and one or more lipophilic groups covalently bonded to the reporter molecule through a linker wherein the lipophilic groups, when present in a live cell, are cleaved resulting in one or more negatively charged groups;
   incubating the sample for a period of time sufficient for the compound to enter the cell;
   cleaving the one or more lipophilic groups; and
   illuminating the sample with an appropriate wavelength, whereby the intracellular ions are identified.

41. A composition comprising an intracellular metal ion and an intracellular ion indicator compound, wherein the compound comprises a metal chelating moiety ($M_c$), a reporter molecule and two or more lipophilic groups ($G_L$) covalently bonded through a linker to the reporter molecule, wherein the lipophilic groups, when present in a live cell, are cleaved resulting in two or more negatively charged groups.

42. A kit for binding an intracellular metal ion in a sample, comprising:
   a intracellular ion indicator compound, wherein the compound comprises a metal chelating moiety ($M_c$), a reporter molecule and two or more lipophilic groups ($G_L$) covalently bonded through a linker to the reporter molecule, wherein the lipophilic groups, when present in a live cell, are cleaved resulting in two or more negatively charged groups; and
   one or more components selected from the group consisting of a calibration standard of the intracellular metal ion, an ionophore, a fluorescent standard, an aqueous buffer solution and an organic solvent.

43. A method of making a cell permeable compound, wherein the compound comprises a metal chelating moiety ($M_c$), a reporter molecule and two or more lipophilic groups ($G_L$) covalently bonded through a linker to the reporter molecule, wherein the lipophilic groups, when present in a live cell, are cleaved resulting in two or more negatively charged groups, the method comprising:
   contacting the metal ion chelator ($M_c$) with the reporter molecule, such that the reporter molecule covalently binds to the metal ion chelator; and
   contacting a lipophilic group with a negatively charged substituent present on the reporter molecule, such that the lipophilic group binds to the negatively charged group thereby neutralizing the negatively charged group.

44. A compound selected from the group consisting of:

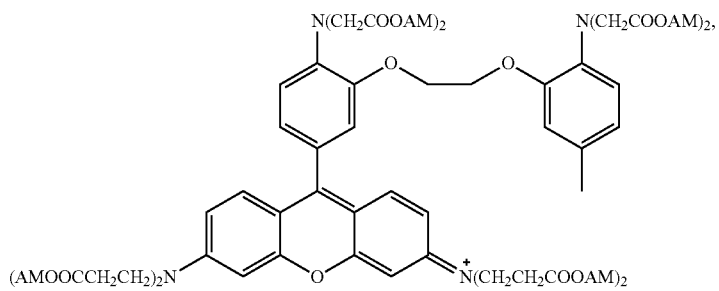

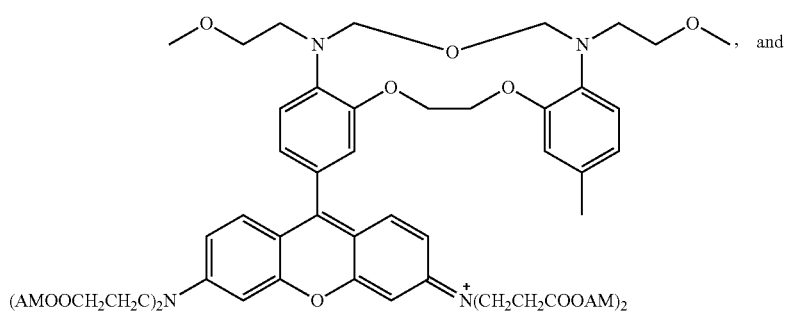

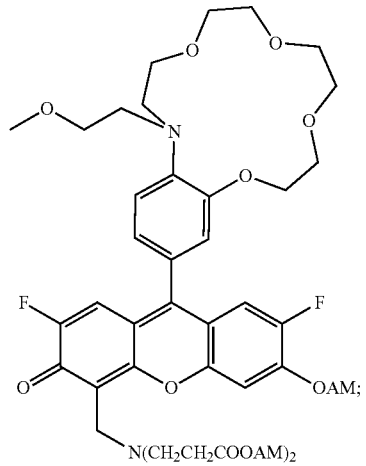
wherein AM is —CH$_2$OC(=O)CH$_3$.
45. A compound selected from the group consisting of:
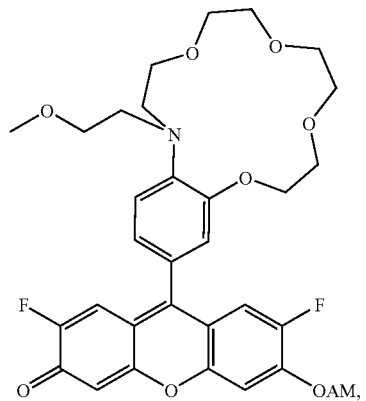
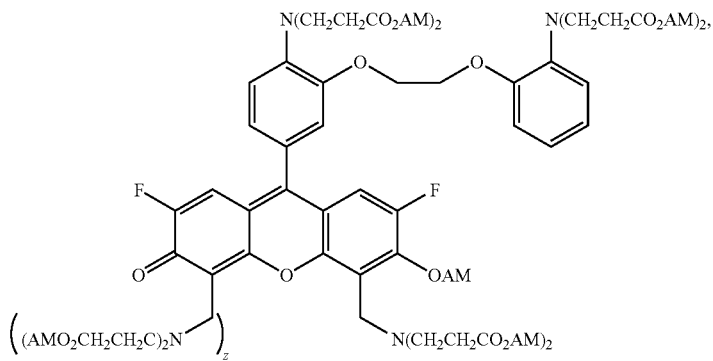

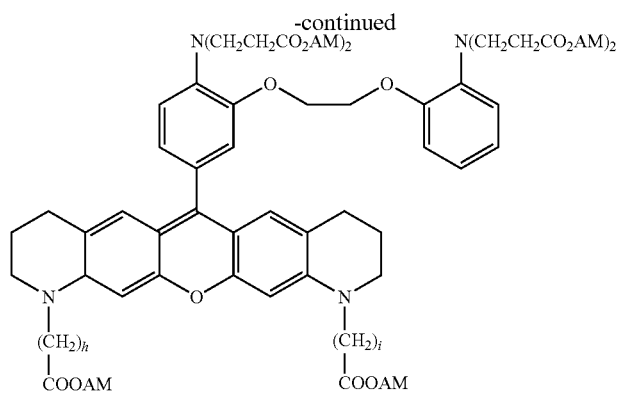
wherein h and i are independently 0-4;
z is 0 or 1; and
AM is —CH$_2$OC(═O)CH$_3$.

UNITED STATES PATENT AND TRADEMARK OFFICE
CERTIFICATE OF CORRECTION

PATENT NO. : 8,318,502 B2  Page 1 of 2
APPLICATION NO. : 12/602973
DATED : November 27, 2012
INVENTOR(S) : Kyle Gee et al.

It is certified that error appears in the above-identified patent and that said Letters Patent is hereby corrected as shown below:

In the Claims:

In claim 1 at column 51, line 52, delete "GO", and insert --GL--, therefor.

In claim 17 at column 52, line 65, delete "0", and insert --O--, therefor.

In claim 22 at column 54, line 7, delete "II", and insert --H--, therefor.

In claim 44, delete

" 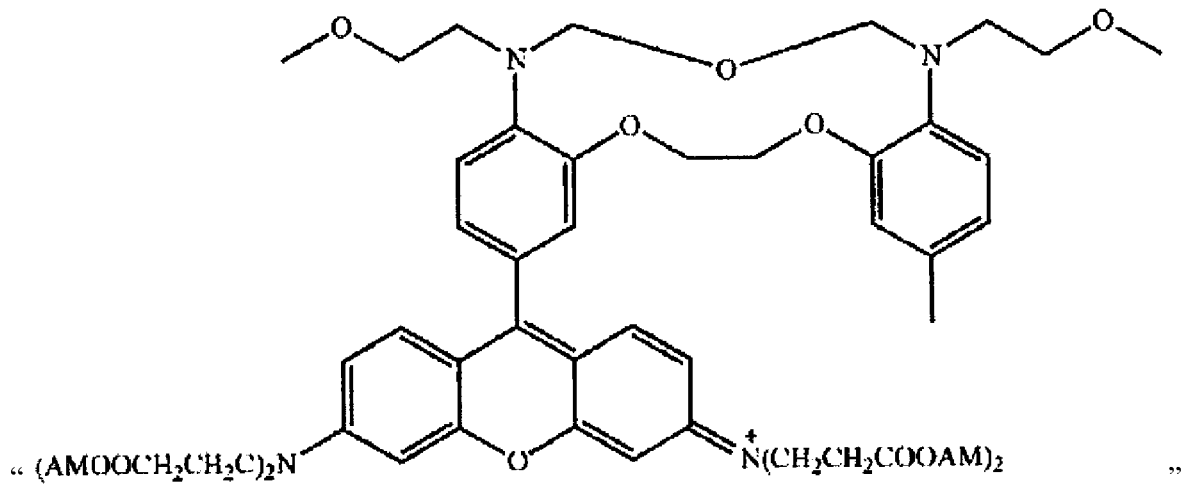 "

Signed and Sealed this
Eleventh Day of November, 2014

*Michelle K. Lee*
Michelle K. Lee
*Deputy Director of the United States Patent and Trademark Office*

CERTIFICATE OF CORRECTION (continued)
U.S. Pat. No. 8,318,502 B2 and insert

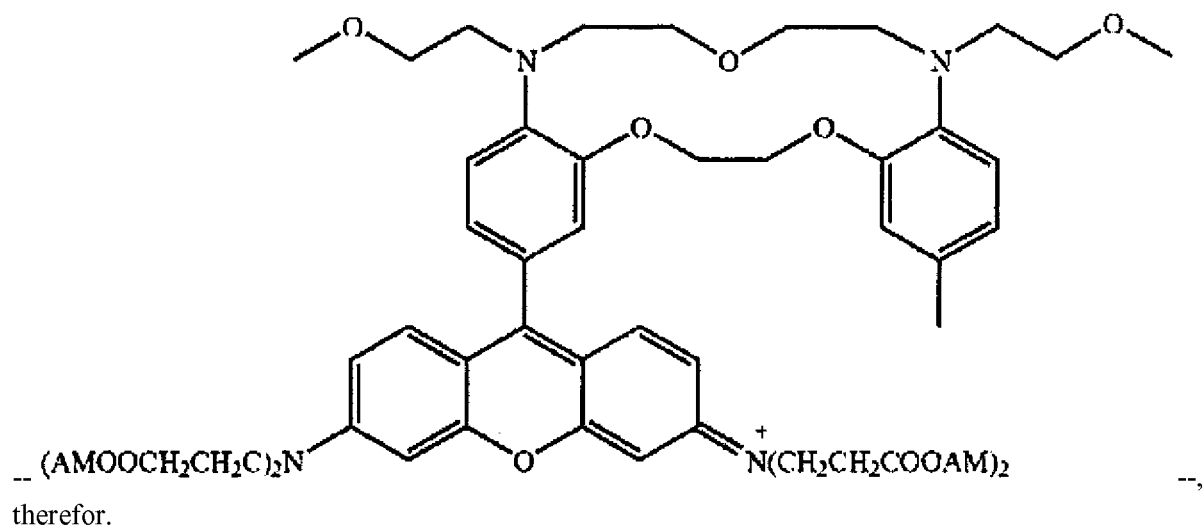

therefor.